United States Patent
Deshpande et al.

(10) Patent No.: US 8,986,676 B2
(45) Date of Patent: Mar. 24, 2015

(54) MNTF DIFFERENTIATION AND GROWTH OF STEM CELLS

(75) Inventors: Deepa M. Deshpande, Baltimore, MD (US); Douglas A. Kerr, Ruxton, MD (US); Dorothy Pui-Yuk Ko, Monterey Park, CA (US)

(73) Assignee: Genervon Biopharmaceuticals LLC, Pasadena, CA (US)

( * ) Notice: Subject to any disclaimer, the term of this patent is extended or adjusted under 35 U.S.C. 154(b) by 931 days.

(21) Appl. No.: 12/093,452

(22) PCT Filed: Nov. 10, 2006

(86) PCT No.: PCT/US2006/043874
§ 371 (c)(1),
(2), (4) Date: May 13, 2008

(87) PCT Pub. No.: WO2007/058982
PCT Pub. Date: May 24, 2007

(65) Prior Publication Data
US 2009/0117085 A1    May 7, 2009

Related U.S. Application Data

(60) Provisional application No. 60/735,702, filed on Nov. 10, 2005, provisional application No. 60/841,766, filed on Sep. 1, 2006, provisional application No. 60/858,022, filed on Nov. 10, 2006.

(51) Int. Cl.
*A61K 35/12*    (2006.01)
*A61K 38/17*    (2006.01)

(52) U.S. Cl.
CPC ................. *A61K 38/1703* (2013.01)
USPC ............. 424/93.7; 435/377; 514/1.1

(58) Field of Classification Search
CPC .... C07K 14/475; C07K 14/48; A61K 38/185; A61K 38/1703
USPC ........ 514/8.3, 8.4, 17.7, 18.9, 21.8; 424/93.7; 435/377
See application file for complete search history.

(56) References Cited

U.S. PATENT DOCUMENTS 6,309,877 B1 * 10/2001 Chau ............................ 435/325
2002/0086831 A1 * 7/2002 Chau ............................ 514/12

OTHER PUBLICATIONS

Kawasaki et al. Generation of dopaminergic neurons and pigmented epithelia from primate ES cells by stromal cell-derived inducing activity. Proc Natl Acad Sci U S A. Feb. 5, 2002;99(3):1580-5. Epub Jan. 29, 2002.*
Gepstein et al. Derivation and potential applications of human embryonic stem cells. Circ Res. Nov. 15, 2002;91(10):866-76.*
Verfaillie et al. Stem cells: hype and reality. Hematology Am Soc Hematol Educ Program. 2002:369-91.*
Hoffman et al. Characterization and culture of human embryonic stem cells. Nat Biotechnol. Jun. 2005;23(6):699-708.*
Schuldiner et al. Effects of eight growth factors on the differentiation of cells derived from human embryonic stem cells. Proc Natl Acad Sci U S A. Oct. 10, 2000;97(21):11307-12.*
Sato et al. Maintenance of pluripotency in human and mouse embryonic stem cells through activation of Wnt signaling by a pharmacological GSK-3-specific inhibitor. Nat Med. Jan. 2004;10(1):55-63. Epub Dec. 21, 2003.*
Humphrey et al. Maintenance of pluripotency in human embryonic stem cells is STAT3 independent. Stem Cells. 2004;22(4):522-30.*
Li et al. Bone morphogenetic protein 4 induces efficient hematopoietic differentiation of rhesus monkey embryonic stem cells in vitro. Blood. Jul. 15, 2001;98(2):335-42.*

* cited by examiner

*Primary Examiner* — Gregory S Emch

(57) ABSTRACT

The present invention provides methods for inducing differentiation of an embryonic stem cell into a motor neuron using a motoneuronotrophic factor (MNTF) or its peptide analogs. The present invention further provides a method for isolating a population of stem cell derived motor neurons and a population of cells comprising the differentiated neural cells. Additionally, the present invention is directed to a method of enhancing the survival of the differentiated neural cells in long term cell cultures. Finally, the present invention provides compositions containing MNTF or its peptide analogs for therapeutic use in conjunction with stem cells.

22 Claims, 8 Drawing Sheets

FIG. 1

| | | |
|---|---|---|
| SEQ ID NO:1 | 33-mer | LGTFWGDTLNCWMLSAFSRYARCLAEGHDGPTQ |
| SEQ ID NO:2 | 6-mer | FSRYAR |
| SEQ ID NO:3 | 7-mer | WMLSAFS |
| SEQ ID NO:4 | 10-mer | MLSAFSRYAR |
| SEQ ID NO:5 | 11-mer | FSRYARCLAEG |
| SEQ ID NO:6 | 13-mer | CWMLSAFSRYARC |
| SEQ ID NO:7 | 21-mer | MLSAFSRYARCLAEGHDGPTQ |

SEQUENCE LISTING

<160> NUMBER OF SEQ ID NOS: 7

<210> SEQ ID NO 1
<211> LENGTH: 33
<212> TYPE: PRT
<213> ORGANISM: Artificial
<220> FEATURE:
<223> OTHER INFORMATION: Synthetic peptide
<220> FEATURE:
<221> NAME/KEY: 33-mer MNTF
<222> LOCATION: (1)..(33)
<223> OTHER INFORMATION: synthetic peptide

<400> SEQUENCE: 1

Leu Gly Thr Phe Trp Gly Asp Thr Leu Asn Cys Trp Met Leu Ser Ala
1               5                   10                  15

Phe Ser Arg Tyr Ala Arg Cys Leu Ala Glu Gly His Asp Gly Pro Thr
            20                  25                  30

Gln

<210> SEQ ID NO 2
<211> LENGTH: 6
<212> TYPE: PRT
<213> ORGANISM: artificial sequence
<220> FEATURE:
<223> OTHER INFORMATION: Synthetic MNTF peptide analog
<220> FEATURE:
<221> NAME/KEY: 6-mer peptide analog
<222> LOCATION: (1)..(6)

<400> SEQUENCE: 2

Phe Ser Arg Tyr Ala Arg
1               5

<210> SEQ ID NO 3
<211> LENGTH: 7
<212> TYPE: PRT
<213> ORGANISM: artificial sequence
<220> FEATURE:
<223> OTHER INFORMATION: Synthetic MNTF peptide analog
<220> FEATURE:
<221> NAME/KEY: 7-mer
<222> LOCATION: (1)..(7)
<223> OTHER INFORMATION: peptide analog

<400> SEQUENCE: 3

Trp Met Leu Ser Ala Phe Ser
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic MNTF peptide analog
<220> FEATURE:
<221> NAME/KEY: 10-mer peptide analog
<222> LOCATION: (1)..(10)
<223> OTHER INFORMATION: synthetic peptide

<400> SEQUENCE: 4

Met Leu Ser Ala Phe Ser Arg Tyr Ala Arg
1               5                   10

<210> SEQ ID NO 5
<211> LENGTH: 11
<212> TYPE: PRT
<213> ORGANISM: Artificial sequence

```
<220> FEATURE:
<223> OTHER INFORMATION: Synthetic MNTF peptide analog
<220> FEATURE:
<221> NAME/KEY: 11-mer peptide analog
<222> LOCATION: (1)..(11)

<400> SEQUENCE: 5

Phe Ser Arg Tyr Ala Arg Cys Leu Ala Glu Gly
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic MNTF peptide sequence
<220> FEATURE:
<221> NAME/KEY: 13-mer
<222> LOCATION: (1)..(13)
<223> OTHER INFORMATION: synthetic peptide

<400> SEQUENCE: 6

Cys Trp Met Leu Ser Ala Phe Ser Arg Tyr Ala Arg Cys
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Synthetic MNTF peptide analog
<220> FEATURE:
<221> NAME/KEY: 21-mer
<222> LOCATION: (1)..(21)
<223> OTHER INFORMATION: synthetic peptide

<400> SEQUENCE: 7

Met Leu Ser Ala Phe Ser Arg Tyr Ala Arg Cys Leu Ala Glu Gly His
1               5                   10                  15

Asp Gly Pro Thr Gln
            20
```

MNTF DIFFERENTIATION AND GROWTH OF STEM CELLS

RELATED APPLICATIONS

This application takes priority from U.S. provisional application No. 60/735,702, filed Nov. 10, 2005, entitled "MNTF Differentiation and Growth of Stem Cells"; U.S. provisional application No. 60/841,766, filed Sep. 1, 2006, entitled "Motoneuron Tropic factor Differentiates Murine Embryonic Stem Cells Into Motor Neurons Independent of the Sonic Hedgehog Receptor"; and U.S. provisional application No. 60/858,022, filed Nov. 10, 2006, entitled "Methods of Treating Neuronal Disorders using MNTF peptides and analogues thereof" incorporated by reference herein in their entirety.

BACKGROUND OF INVENTION

The following includes information that may be useful in understanding the present inventions. It is not an admission that any of the information provided herein is prior art, or relevant, to the presently described or claimed inventions, or that any publication or document that is specifically or implicitly referenced is prior art.

Until recently, a persistent dogma of neuroscience was that neurons in the adult human brain and spinal cord could not regenerate. However, in the mid-1990s, neuroscientists learned that some parts of the adult human brain do, in fact, generate new neurons. These new neurons arise from "neural stem cells" in the fetal as well as the adult brain. The discovery of a regenerative capacity in the adult central nervous system holds out promise that it may eventually be possible to repair damage from neurodegenerative diseases such as amyotrophic lateral sclerosis (ALS, also known as Lou Gehrig's disease), as well as from brain and spinal cord injuries resulting from stroke or trauma. However, the non-invasive isolation and purification of significant numbers of neural stem cells from the brain remain challenging.

On the other hand, embryonic stem (ES) cells are pluripotent cells that are both self-renewing and have the capacity to differentiate into any cell type in the human organism. They can be propagated in vitro for long periods of time in an undifferentiated state and thus represent an attractive source of cells for developmental studies and for therapy of human diseases.

ES cells are responsive to environmental cues upon transplantation and adopt a cellular fate that is appropriate to the transplanted region. Nevertheless, the dependence on environmental cues to direct stem cells precludes the efficient generation of neurons in non-neurogenic regions of the CNS.

Recently, it has become possible to direct the differentiation of stem cells ex vivo, theoretically making these cells less dependent or independent of in vivo cues. For example, spinal motorneurons can be generated efficiently by exposing mouse ES cells to retinoic acid (RA) and Sonic Hedgehog. In this paradigm, RA serves both to neuralize and to establish a caudal positional identity for the pluripotent ES cells. Sonic hedgehog or Hedgehog agonist (HhAg1.3) further specifies a ventral positional identity and in response, a substantial proportion of ES cells initiate a motor neuron-specific transcriptional pattern and acquire immunohistochemical features of mature neurons. ES cell-derived motoneurons transplanted into embryonic chick spinal cord extend axons into the periphery and form neuromuscular junctions. [Wichterle, H., Lieberam, I., Porter, J. A. & Jessel, T. M. Directed differentiation of embryonic stem cells into motor neurons. Cell 110, 385-397 (2002)].

The therapeutic potential of embryonic stem (ES) cells is promising, but in many cases limited by our inability to promote differentiation to specific cell types, such as motor neurons. Accordingly, there is a pressing need for technology to generate more homogenous differentiated cell populations from pluripotent stem cells.

The isolation and characterization of two motoneuronotrophic factors (MNTF1 and MNTF2) from rat muscle tissues as well as the subsequent cloning of a recombinant MNTF1-F6 gene derived from a human retinoblastoma cDNA library, is described in U.S. Pat. Nos. 6,309,877, 6,759,389 and 6,841,531 (as well as co-pending U.S. patent application Ser. Nos. 10/858,144, 10/858,286, 10/858,543 and 10/858,545). Nucleotide sequences encoding polypeptides related to MNTF1, were found to map within human chromosome 16q22, as described in International Application No. PCT/US2004/038651.

The MNTF1-F6 gene sequence encodes a 33 amino acid sequence. The naturally occurring and recombinant MNTF1 polypeptides were shown to selectively enhance the survival in vitro of anterior horn motor neurons isolated from rat lumbar spinal cord explants. Photomicrographs of treated cultures exhibited neurite outgrowth of myelinated nerve fibers and a marked reduction in the growth of non-neuronal cells, e.g. glial cells and fibroblasts. Similarly, in vivo administration of MNTF1 to surgically axotomized rat peripheral nerves resulted in a markedly higher percentage of surviving motor neurons than untreated controls, which could be blocked by co-administration of anti-MNTF1 monoclonal antibody.

Further beneficial effects of MNTF1 were demonstrated in rats subjected to spinal cord hemi-section, repaired by a peripheral nerve autograft and implanted with MNTF1-containing gel sections in close proximity to the nerve graft junctions with spinal cord. MNTF1 treated animals exhibited greater numbers of surviving motor neurons, improved recovery of motor and sensory function, reduced inflammatory response (fewer infiltrating macrophages and lymphocytes) and reduced collagen-containing scar tissue formation at the site of the graft, normal Schwann cell morphology and normal myelinated and non-myelinated nerve fiber formation.

The efficacy of MNTF in the treatment of neurodegenerative disease was also demonstrated in the wobbler mouse animal model. Wobbler mice carry an autosomal double-recessive gene mutation that leads to the progressive degeneration of spinal and brain stem motor neurons. Implantation of MNTF1-containing gel sections between the trapezius and rhomboid muscles and the C7-T3 region of the spinal cord delayed the progression of symptoms in wobbler mice, resulting in a general improvement in life span, health, respiration, body weight, strength of forelimbs as well as reduced vacuolation and chromatolysis of their cervical motor neurons compared to the control group.

Two overlapping domains within the MNTF1-F6 molecule that appear to be sufficient for the known biological activities of MNTF1 were identified. See, International Application No. PCT/US04/01468 or U.S. patent application Ser. No. 10/541,343. Each of these domains, designated herein as the "WMLSAFS" and "FSRYAR" domains, were sufficient to stimulate the proliferation of motor neuron derived cell lines in a manner similar to the MNTF1-F6 33-mer. Similarly, the "FSRYAR" domain is sufficient to direct selective reinnervation of muscle targets by motor neurons in vivo in a manner similar to the MNTF1-F6 33-mer. In addition, the "FSRYAR" domain provides an antigenic epitope sufficient to raise antibody that recognizes any MNTF peptide containing the "FSRYAR" sequence, including the MNTF1-F6 33-mer.

Clearly, more efficient and selective methods are needed to direct the proliferation and the differentiation of stem cells, especially ES cells, to produce homogenous populations of motor neurons. This may be important not only for the therapeutic use of stem cells in the treatment of neurodegenerative disorders, but will also greatly facilitate studies of the molecular mechanism of development.

SUMMARY OF THE INVENTION

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

Here we describe the successful differentiation of ES cells to cells exhibiting molecular markers characteristic of mature motor neurons using MNTF or MNTF peptide analogues. The invention provides compositions, methods, and a system for preparing and characterizing stem cell-derived motor neurons suitable for use for therapeutic administration and drug screening.

The present invention also provides compositions containing MNTF peptides for therapeutic stem cell applications or as cell culture media suitable for the differentiation and maintenance of stem cell derived motor neurons. Applications for stem cells include the treatment of neuronal disorders, such as the improvement of motor function.

The invention includes methods of treating a neuronal disorder. In certain embodiments, these methods comprise administering a motoneuronotropic factor (MNTF) peptide or analogue thereof to a patient to modulate a signaling pathway to ameliorate or inhibit the progression of the neuronal disorder. In a preferred embodiment of this method, the MNTF peptide is a MNTF analogue that is 6 to 35 amino acids in length, between 6 and 33 amino acids in length, 33 amino acids in length (e.g. SEQ ID NO:1), 6 amino acids in length (e.g. SEQ ID NO:2), 7 amino acids in length (e.g. SEQ ID NO:3), 10 amino acids in length (e.g. SEQ ID NO:4), 11 amino acids in length (e.g. SEQ ID NO:5), or another length. In another aspect, methods are provided that comprise administering a peptide that is at least 70%, at least 75%, at least 80%, at least 85%, at least 90%, or at least 95% identical to SEQ ID NO: 1, SEQ ID NO:2, SEQ ID NO:3, SEQ ID NO:4, SEQ ID NO:5, or another peptide described herein.

In addition to the treatment of a neuronal disorder, the invention further includes methods of promoting the survival, growth, proliferation, or maintenance of mammalian neurons. In another aspect, MNTF or a MNTF analogue functions as a neuroprotective agent. In another aspect, the MNTF or a MNTF analogue modulates a particular differentiation pathway of a cell. In another aspect, the MNTF or a MNTF analogue modulates a protein kinase pathway or modulates the expression or activity of a tyrosine kinase or growth factor receptor. A signal transduction or protein kinase pathway that is regulated may include, for example, a sonic hedgehog independent pathway, a sonic hedgehog dependent pathway, or a combination of these.

In certain preferred embodiments, the MNTF or a MNTF analogue modulates a pathway that is at independent of the sonic hedgehog pathway. Such a pathway is generally independent of signal transduction events triggered by the binding of a sonic hedgehog protein to a patched receptor and associated promotion of hedgehog dependent signal transduction. In other embodiments, the MNTF or a MNTF analogue modulates a pathway that is at least partially independent of the sonic hedgehog pathway. Such a pathway is generally partially independent of signal transduction events triggered by the binding of a sonic hedgehog protein to a patched receptor and associated promotion of hedgehog dependent signal transduction.

While not intending on being bound to any theory or mechanism, it is believed that the MNTF or a MNTF analogues provided herein are capable of modulating the expression or activity of one or more of the following: a insulin receptor, IGF-1 receptor, IGF-2 receptor, Shh, Akt, Bad (bcl-2 antagonist of cell death), PI(3,4,5)P3-dependent kinase 1 (PDK1), Bax, p53 gene product, pp60-Src, JAK2, nitric oxide synthases (NOS), glycogen synthase kinase 3 (GSK), caspase, PI3 kinase (phosphatidylinositol 3-kinase), and Ras. In certain embodiments, MNTF of a MNTF analogue modulates the expression or activity of one or more protein which binds to tyrosine-phosphorylated IRS-protein (e.g. IRS-1, IRS-2, IRS-3, and IRS-4). In other embodiments, the expression or activity of one or more of the following is regulated PI3 Kinase, p85, P110, GRB2, SHP2, Nck, Crk, and Fyn.

There are several neuronal disorders and related indications that can be treated by the compositions and methods provided herein which promote the differentiation, maintenance, or survival of a neuron. Disorders and indications believed to benefit from the administration of a MNTF peptide or MNTF analogue provided herein include, for example, the regeneration of peripheral nerves, regeneration of axons in a spinal cord, promoting the differentiation of certain cells, enhancement of the survival of a target neuronal cell, enhancement of cerebral blood flow, treatment of a spinal cord injury, treatment of a neurodegenerative disease, the treatment of a stroke or cerebral ischemia, the treatment of Huntington's disease, the treatment of Parkinson's disease, the treatment of Multiple Sclerosis, the treatment of ALS, the treatment of Alzheimer's, the treatment of a Diabetic Neuropathy. Another beneficial characteristic of the compositions and methods provided herein is the ability to penetrate the blood brain barrier. Treatment of these neuronal disorders is further described in co-pending application U.S. Ser. No. (to be assigned), filed Nov. 10, 2006, by Ko, Dorothy Tiu-Yak, entitled "Methods of Treating Neuronal Disorders using MNTF peptides and analogues thereof" incorporated by reference herein in its entirety. The present invention also provides compositions and method for the treatment of conditions and disorders associated with neuronal disorders.

Additionally, the present invention provides a method for repopulating a spinal cord with stem cell derived motor neurons and a method for treating nervous tissue degeneration in a subject in need of treatment.

It has been discovered that when pluripotent stem cells are cultured in the presence of selected differentiating agents, such as RA and MNTF peptide analogues alone or in combination, a population of cells is derived that has a remarkably high proportion of cells with phenotypic characteristics of motor neurons. Optionally, the proportion of neural cells can be enhanced by sorting differentiated cells according to molecular markers specific for motor neurons. Since certain types of pluripotent stem cells (such as embryonic stem cells) can proliferate in culture for a year or more, the invention described in this disclosure provides an almost limitless supply of stem cell derived motor neurons.

The present invention provides a method for inducing differentiation of an embryonic stem cell into stem cell progeny (e.g. a differentiated motor neuron). In one embodiment, the first step is obtaining or generating a culture of embryonic stem cells. The next step is contacting the culture of embryonic stem cells with an amount of retinoic acid effective to produce neural progenitor cells and an amount of a MNTF peptide analogue effective to produce motor neurons. In another embodiment, the present invention is directed to enhancing the survival of stem cell derived motor neurons using MNTF or its analogue as a growth supplement in cell cultures.

The present invention further provides a population of cells comprising the stem cell derived motor neurons and uses of same.

The present invention is further directed to a method for isolating a population of stem cell derived motor neurons.

Also provided are materials and methods of transplanting differentiated neural stem cell progeny (e.g. motor neurons) into a host. A method according to one embodiment comprises the steps of i) obtaining a population of cells derived from a mammalian neural tissue containing at least one multipotent CNS neural stem cell; ii) culturing the neural stem cell in a culture medium comprising a motoneuronotropic factor (MNTF) analogue 6 to 35 amino acids in length which under suitable culture conditions induces multipotent neural stem cell proliferation; iii) inducing proliferation of said multipotent neural stem cell to produce neural stem cell progeny which includes multipotent neural stem cell progeny cells; and iv) transplanting said neural stem cell progeny to the host.

DESCRIPTION OF THE FIGURES

The present invention may be better understood and its advantages appreciated by those individuals skilled in the relevant art by referring to the accompanying figures wherein:

FIG. 1 shows the amino acid sequences of the MNTF peptides tested;

DETAILED DESCRIPTION

Definitions

Figure 2:
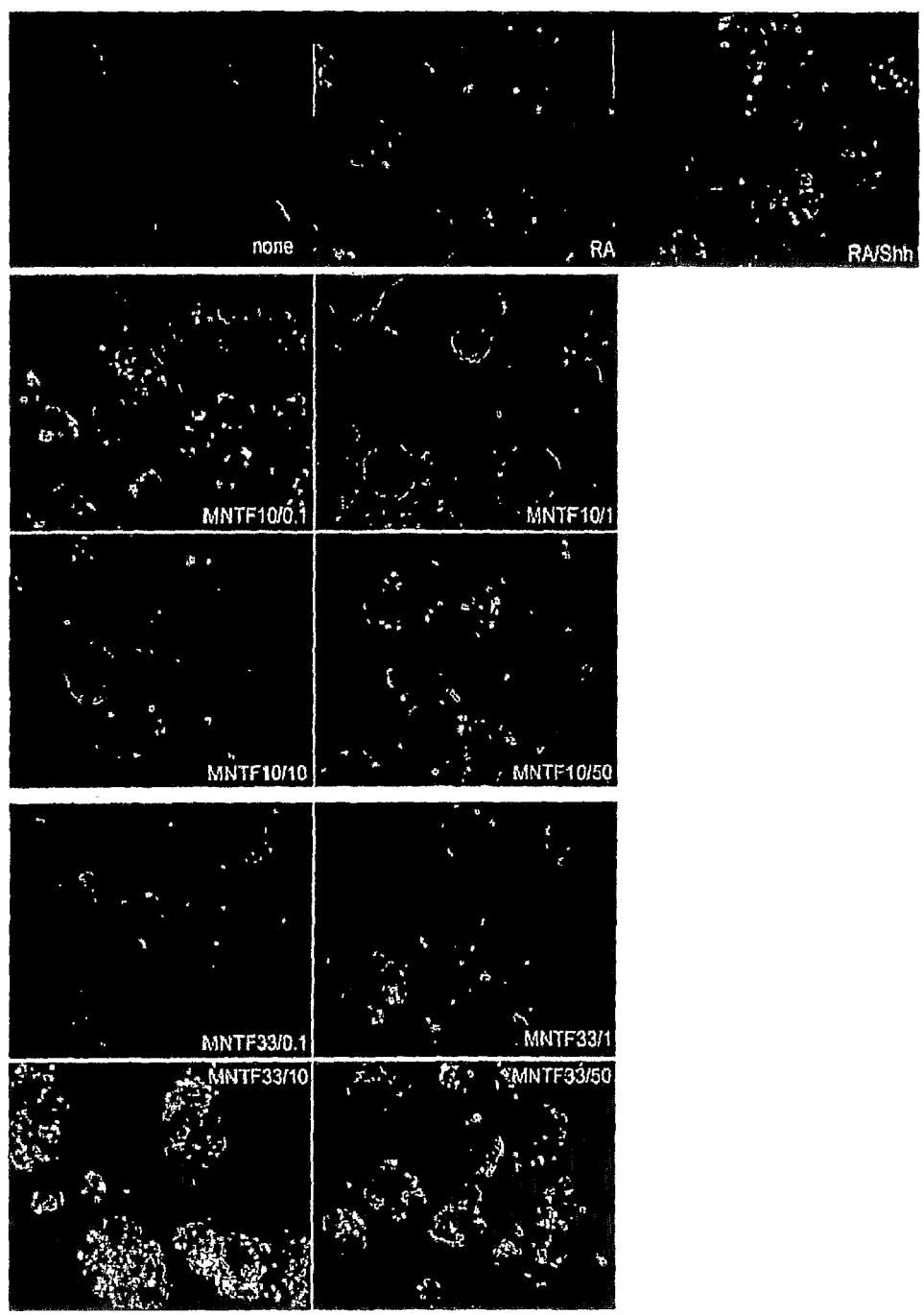
FIG. 2 compares the expression of GFP fluorescence under the control of the motor neuron specific HB9 promoter in response to retinoic acid (RA), retinoic acid and sonic hedgehog (RA/Shh), retinoic acid and MNTF 10-mer (SEQ ID NO:4) at 0.1 μg/ml-50 μg/ml (MNTF 10/0.1-50) and MNTF 33-mer (SEQ ID NO:1) at 0.1 μg/ml-50 μg/ml (MNTF 33/0.1-50)

Before further describing the inventions in general and in terms of various nonlimiting specific embodiments, certain terms used in the context of the describing the invention are set forth. Unless indicated otherwise, the following terms have the following meanings when used herein and in the appended claims. Those terms that are not defined below or elsewhere in the specification shall have their art-recognized meaning.

Amino acids used in compounds provided herein (e.g. peptides and proteins) can be genetically encoded amino acids, naturally occurring non-genetically encoded amino acids, or synthetic amino acids. Both L- and D-enantiomers of any of the above can be utilized in the compounds. The following abbreviations may be used herein for the following genetically encoded amino acids (and residues thereof): alanine (Ala, A); arginine (Arg, R); asparagine (Asn, N); aspartic acid (Asp, D); cyteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V).

Certain commonly encountered amino acids that are not genetically encoded and that can be present in the compounds of the invention include, but are not limited to, β-alanine (b-Ala) and other omega-amino acids such as 3-aminopropionic acid (Dap), 2,3-diaminopropionic acid (Dpr, Z), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle, J); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys); 3-benzothiazol-2-yl-alanine (BztAla, B); and homoserine (hSer). Additional amino acid analogs contemplated include phosphoserine, phosphothreonine, phosphotyrosine, hydroxyproline, gamma-carboxyglutamate, hippuric acid, octahydroindole-2-carboxylic acid, statine, α-methylalanine, para-benzoyl-phenylalanine, propargylglycine, and sarcosine. Peptides that are encompassed within the scope of the invention can have any of the foregoing amino acids in the L- or D-configuration, or any other amino acid described herein or known in the art, whether currently or in the future.

Amino acids that are substitutable for each other generally reside within similar classes or subclasses. As known to one of skill in the art, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. Polar amino acids include amino acids having acidic, basic or hydrophilic side chains and nonpolar amino acids include amino acids having aromatic or hydrophobic side chains. Nonpolar amino acids may be further subdivided to include, among others, aliphatic amino acids. The definitions of the classes of amino acids as used herein are as follows:

"Nonpolar Amino Acid" refers to an amino acid having a side chain that is uncharged at physiological pH, that is not polar and that is generally repelled by aqueous solution. Examples of genetically encoded hydrophobic amino acids include Ala, Ile, Leu, Met, Trp, Tyr and Val. Examples of non-genetically encoded nonpolar amino acids include t-BuA, Cha and Nle.

"Aromatic Amino Acid" refers to a nonpolar amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 3-benzothiazol-2-yl-alanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic Amino Acid" refers to a nonpolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Polar Amino Acid" refers to a hydrophilic amino acid having a side chain that is charged or uncharged at physiological pH and that has a bond in which the pair of electrons shared in common by two atoms is held more closely by one of the atoms. Polar amino acids are generally hydrophilic, meaning that they have an amino acid having a side chain that is attracted by aqueous solution. Examples of genetically encoded polar amino acids include asparagine, cysteine, glutamine, lysine and serine. Examples of non-genetically encoded polar amino acids include citrulline, homocysteine, N-acetyl lysine and methionine sulfoxide.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include ornithine, 2,3-diaminopropionic acid, 2,4-diaminobutyric acid and homoarginine.

"Ionizable Amino Acid" refers to an amino acid that can be charged at a physiological pH. Such ionizable amino acids include acidic and basic amino acids, for example, D-aspartic acid, D-glutamic acid, D-histidine, D-arginine, D-lysine, D-hydroxylysine, D-ornithine, L-aspartic acid, L-glutamic acid, L-histidine, L-arginine, L-lysine, L-hydroxylysine or L-ornithine.

As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar, aromatic and polar. However, the nonpolar ring is dominant and so tyrosine is generally considered to be nonpolar. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

In some embodiments, polar amino acids contemplated by the present invention include, for example, arginine, asparagine, aspartic acid, cysteine, glutamic acid, glutamine, histidine, homocysteine, lysine, hydroxylysine, ornithine, serine, threonine, and structurally related amino acids. In one embodiment the polar amino is an ionizable amino acid such as arginine, aspartic acid, glutamic acid, histidine, hydroxylysine, lysine, or ornithine.

Examples of polar or nonpolar amino acid residues that can be utilized include, for example, alanine, valine, leucine, methionine, isoleucine, phenylalanine, tryptophan, tyrosine and the like.

As used herein, the terms "biologically active peptide" and "biologically active fragment" refer to a peptide or polypeptide in accordance with the above description of motoneuron differentiation factors (MNDF) or motoneuronotrophic factors (MNTF) wherein the MNDF differentiates stem cells into motor neurons and the MNTF exhibits a protective or proliferative effect on stem cell derived motor neurons.

A "cell" means any living cell suitable for the desired application. Cells include eukaryotic and prokaryotic cells.

The term "complementary" generally refers to the natural binding of polynucleotides by base pairing, for example under permissive salt and temperature conditions. For example, the sequence "A-G-T" binds to the complementary sequence "T-C-A". Complementarity between two single-stranded molecules may be "partial", such that only some of the nucleic acids bind, or it may be "complete", such that total complementarity exists between the single stranded molecules. The degree of complementarity between nucleic acid molecules has significant effects on the efficiency and strength of the hybridization between them. "Hybridizable" and "complementary" are terms that are used to indicate a sufficient degree of complementarity such that binding, preferably stable binding sufficient to carry out an intended action, for example, occurs between nucleic acids. It is understood that an oligonucleotide need not be 100% complementary to its target nucleic acid sequence to be hybridizable.

The term "composition" is intended to encompass a product comprising one or more ingredients.

The term "differentiated" is a relative term in which a "differentiated cell" is a cell that has progressed further down the developmental pathway than the cell it is being compared against. As further used herein, a "differentiated neural cell" generally refers to a partially-differentiated or fully-differentiated cell of the central nervous system (CNS) or peripheral nervous system (PNS). Progenitor cells are parent cells which, during development and differentiation, give rise to a distinct cell lineage by a series of cell divisions. Neural progenitor cells, for example, are committed to a cell lineage that will develop, eventually, into fully-differentiated neural cells of the CNS or PNS; however, such neural progenitor cells may not yet be dedicated to a particular type, or subclass, of neural cell. Neural progenitor cells may become committed to a cell line that will differentiate into a specific type of neural cell, and, thereafter, give rise to fully-differentiated neural cells. Accordingly, the partially-differentiated neural cell of the present invention may be a cell, with a neural identity, that has acquired a directional or positional character, or that has committed to developing into a particular class of neural cell, but is not a fully-differentiated neural cell. For example, treatment of ES cells with an MNTF peptide, alone or in combination with a morphogen, such as RA, can give rise to a partially differentiated neural cell or neural progenitor cell in accordance with the present invention.

A "disorder" is any condition that would benefit from treatment with a molecule or composition of the invention, including those described or claimed herein. This includes chronic and acute disorders or diseases including those pathological conditions that predispose the mammal to the disorder in question.

"Feeder cells" or "feeders" include cells of one type that are co-cultured with cells of another type, generally to provide an environment in which the cells of the second type can grow. For example, certain types of pPS cells can be supported by primary mouse embryonic fibroblasts, immortalized mouse embryonic fibroblasts, or human fibroblast-like cells differentiated from hES cell.

By "functional equivalent" is meant a peptide possessing a biological activity substantially similar to that of the M L S A F S R Y A R domain(s), and is intended to include "fragments", "variants", "analogs", "homologs", or "chemical derivatives" possessing such activity or characteristic. Functional equivalents of the M L S A F S RY A R domain(s), then, may not share an identical amino acid sequences, and conservative or non-conservative amino acid substitutions of conventional or unconventional amino acids are possible.

The term "gene product" refers to an RNA molecule transcribed from a gene, or a polypeptide encoded by the gene or translated from the RNA.

A "growth environment" is an environment in which cells of interest can proliferate, differentiate, or mature in vitro under appropriate conditions. Such conditions may include, for example, the medium in which the cells are cultured, any growth factors or differentiation-inducing factors that may be present, and a solid surface or supporting structure.

As used herein, the term "M L S A F S R Y A R domain" refers to a polypeptide domain demonstrated herein to be sufficient for the differentiation of stem cells into motor neurons, and to peptides and/or molecules capable of mimicking their structure and/or function. Preferred versions of the present invention utilize a peptide comprising the amino acid sequence: M L S A F S R Y A R, as well as functional equivalents thereof.

The terms "modulator" and "modulation" as used herein in its various forms is intended to encompass inhibition in whole or in part of the expression or action or activity of a particular target.

As used herein, a "motoneuronotrophic factor" includes those factors involved in the nutrition or maintenance of motor neurons. The terms "motoneuronotropic factor", "MNTF", "MNTF peptide", "motoneuronotropic factor analogue", and "MNTF analogue" may be used interchangeably as long as they have the functional properties defined herein. Motoneuronotrophic factors, may further the development and differentiation of committed neural progenitor cells, or they may induce or enhance the growth (e.g. nurite outgrowth) and survival of differentiated neural cells. The motoneuronotrophic factors of the present invention are typically provided in amounts effective to produce a fully-differentiated neural cell of the CNS or PNS (e.g., a motor neuron). Guidance for the amount is provided herein, and may be readily determined by the skilled artisan based upon known procedures and methods disclosed herein.

For the purposes of this disclosure, the terms "neural progenitor cell" or "neural precursor cell" include a cell that can generate progeny that are either neuronal cells (e.g. neuronal precursors or mature neurons) or glial cells (e.g. glial precursors, mature astrocytes, or mature oligodendrocytes). The cells typically express some of the phenotypic markers that are characteristic of the neural lineage, and they do not generally produce progeny of other embryonic germ layers when cultured alone in vitro.

A "neuronal progenitor cell" or "neuronal precursor cell" include a cell that can generate progeny that are mature neurons and sometimes also have the capability to generate glial cells.

A "multipotent neural progenitor cell population" includes a cell population that has the capability to generate both progeny that are neuronal cells, progeny that are glial cells, and sometimes other types of cells. This term does not require that individual cells within the population have the capability of forming both types of progeny, although individual cells that are multipotent neural progenitors may be present.

The terms "peptidomimetic" and "mimetic" include naturally occurring and synthetic chemical compounds that may have substantially the same structural and functional characteristics of protein regions which they mimic.

Peptide analogs with properties analogous to those of the template peptide may be non-peptide drugs. "Peptide mimetics" or "peptidomimetics," which include peptide-based compounds, also include such non-peptide based compounds (Fauchere, *J. Adv. Drug Res.* 15: 29 (1986); Veber and Freidinger; TINS; 392 (1985); and Evans et al., *J. Med. Chem.* 30: 1229 (1987); Beeley N., *Trends Biotechnol*. June; 12(6): 213-6 (1994); Kieber-Emmons T, et al.; *Curr Opin Biotechnol*. August; 8(4): 435-41 (1997). Peptide mimetics that are structurally similar to therapeutically useful peptides may be used to produce an equivalent or enhanced therapeutic or prophylactic effect. Generally, peptidomimetics are structurally identical or similar to a paradigm polypeptide (i.e., a polypeptide that has a biological or pharmacological function or activity), but can also have one or more peptide linkages optionally replaced by a linkage selected from the group consisting of, for example, —CH$_2$NH—, —CH$_2$S—, —CH$_2$—CH$_2$—, —CH=CH— (cis and trans), —COCH$_2$—, —CH(OH)CH$_2$—, and —CH$_2$SO—. The mimetic can be either entirely composed of natural amino acids, or non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity.

The phrase "percent (%) identity" refers to the percentage of sequence similarity found in a comparison of two or more sequences. Percent identity can be determined electronically using any suitable software, for example. Likewise, "similarity" between two sequences (or one or more portions of either or both of them) is determined by comparing the sequence of one sequence to a second sequence.

"Pharmaceutically acceptable" compounds and other ingredients of a composition or formulation, for example, a carrier, diluent or excipient, are those that are suitable for administration to a recipient thereof.

In general, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. A "domain" of a protein is also a fragment, and comprises the amino acid residues of the protein often required to confer activity or function.

The term "stringent conditions" refers to conditions that permit hybridization between polynucleotides. Stringent conditions can be defined by salt concentration, the concentration of organic solvent (for example, formamide), temperature, and other conditions well known in the art. Stringency can be increased by reducing the concentration of salt, increasing the concentration of organic solvents, (for example, formamide), or raising the hybridization temperature. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, for example, formamide, while high stringency hybridization can be obtained in the presence of an organic solvent (for example, at least about 35% formamide, most preferably at least about 50% formamide). Stringent temperature conditions will ordinarily include temperatures of at least about 30° C., more preferably of at least about 37° C., and most preferably of at least about 42° C. Varying additional parameters, for example, hybridization time, the concentration of detergent, for example, sodium dodecyl sulfate (SDS), and the inclusion or exclusion of carrier DNA, are well known to those skilled in the art. Various levels of stringency are accomplished by combining these various conditions as needed, and are within the skill in the art. Stringent hybridization conditions may also be defined by conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, for example, Berger and Kimmel, Methods In Enzymology, Vol. 152: *Guide To Molecular Cloning Techniques*, San Diego (1987): Academic Press, Inc. and Sambrook et al., Molecular Cloning (1989): A Laboratory Manual, 2nd Ed., Vols. 1-3, Cold Spring Harbor Laboratory). As indicated by standard references, a simple estimate of the Tm value may be calculated by the equation: Tm=81.5+0.41 (% G+C), when a nucleic acid is in aqueous solution at 1 M NaCl (see for example, Anderson and Young, "Quantitative Filter Hybridization" in Nucleic Acid Hybridization (1985)). The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (for example for example, the presence or absence of formamide, dextran sulfate, polyethylene glycol). The effects of these factors are well known and are discussed in standard references in the art, see for example, Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (for example, 10 to 50 nucleotides) and at least about 60° C. for long probes (for example, greater than 50 nucleotides). As noted, stringent conditions may also be achieved with the addition of destabilizing agents such as formamide, in which case lower temperatures may be employed. In the present invention, the polynucleotide may be a polynucleotide which hybridizes to a target mRNA under conditions of medium to high stringency such as 0.03M sodium chloride and 0.03M sodium citrate at from about 50 to about 60 degrees centigrade.

As used herein, "subject" refers to any animal classified as a mammal, including humans, domestic and farm animals, and zoo, sports, or pet animals, such as dogs, horses, cats, sheep, pigs, cows, etc. The preferred subject is a human.

The term "therapeutically effective amount" means the amount of the subject compound that will elicit a desired response, for example, a biological or medical response of a tissue, system, animal or human that is sought, for example, by a researcher, veterinarian, medical doctor, or other clinician.

"Treatment" refers to both therapeutic treatment and prophylactic or preventive measures. Those in need of treatment include those already with the disorder as well as those in which the disorder is to be prevented.

The term "vector" refers to a nucleic acid molecule amplification, replication, and/or expression vehicle in the form of a plasmid, phage, viral, or other system (be it naturally occurring or synthetic) for the delivery of nucleic acids to cells where the plasmid, phage, or virus may be functional with bacterial, yeast, invertebrate, and/or mammalian host cells. The vector may remain independent of host cell genomic DNA or may integrate in whole or in part with the genomic DNA. The vector will generally but need not contain all necessary elements so as to be functional in any host cell it is compatible with. An "expression vector" is a vector capable of directing the expression of an exogenous polynucleotide, for example, a polynucleotide encoding a binding domain fusion protein, under appropriate conditions.

As described herein, the terms "homology and homologues" include polynucleotides that may be a homologue of sequence in a polynucleotide (e.g. mRNA) of interest. Such polynucleotides typically have at least about 70% homology, preferably at least about 80%, 90%, 95%, 97% or 99% homology with the relevant sequence, for example over a region of at least about 15, 20, 30, 40, 50, 100 more contiguous nucleotides (of the homologous sequence).

Homology may be calculated based on any method in the art. For example the UWGCG Package provides the BESTFIT program which can be used to calculate homology (for example used on its default settings) (Devereux et al., Nucleic Acids Research 12, p387-395 (1984)). The PILEUP and BLAST algorithms can be used to calculate homology or line up sequences (typically on their default settings), for example as described in Altschul S. F.; *J Mol Evol* 36: 290-300 (1993); Altschul, S. F. et al.; *J Mol Biol* 215: 403-10 (1990). Software for performing BLAST analyses is publicly available through the National Center for Biotechnology Information (http://www.ncbi.nlm.nih.gov/L). This algorithm involves first identifying high scoring sequence pair by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff *Proc. Natl. Acad. Sci. USA* 89: 10915-10919 (1992)) alignments (B) of 50, expectation (E) of 10, M=5, N=4, and a comparison of both strands.

The BLAST algorithm performs a statistical analysis of the similarity between two sequences; see e.g., Karlin and Altschul *Proc. Natl. Acad. Sci. USA* 90: 5873-5787 (1993). One measure of similarity provided by the BLAST algorithm is the smallest sum probability (P (N)), which provides an indication of the probability by which a match between two nucleotide or amino acid sequences would occur by chance. For example, a sequence is considered similar to another sequence if the smallest sum probability in comparison of the first sequence is less than about 1, preferably less than about 0.1, more preferably less than about 0.01, and most preferably less than about 0.001.

The homologous sequence typically differs from the relevant sequence by at least (or by no more than) about 1, 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background. Selective hybridization is typically achieved using conditions of medium to high stringency (for example 0.03M sodium chloride and 0.03M sodium citrate at from about 50 degrees C. to about 60 degrees C.). However, such hybridization may be carried out under any suitable conditions known in the art (see Sambrook et al., Molecular Cloning: A Laboratory Manual (1989)). For example, if high stringency is required, suitable conditions include 0.2×SSC at 60 degrees C. If lower stringency is required, suitable conditions include 2×SSC at 60 degrees C.

The term "recombinant" refers to a polynucleotide synthesized or otherwise manipulated in vitro (for example, "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process refers to use of recombinant nucleic acid techniques, for example, involving human intervention in the nucleotide sequence, typically selection or production. Alternatively, it can be a polynucleotide made by generating a sequence comprising a fusion of two or more fragments that are not naturally contiguous to each other. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

A "recombinant host cell" is a cell that contains a vector, for example, a cloning vector or an expression vector, or a cell that has otherwise been manipulated by recombinant techniques to express a protein of interest.

I. Overview

The isolation and characterization of two motoneuronotrophic factors (MNTF1 and MNTF2) from rat muscle tissues as well as the subsequent cloning of a recombinant MNTF1-F6 gene derived from a human retinoblastoma cDNA library, is described in U.S. Pat. Nos. 6,309,877, 6,759,389 and 6,841,531 (as well as co-pending U.S. patent application Ser. Nos. 10/858,144, 10/858,286, 10/858,543 and 10/858,545); all of which are hereby incorporated by reference in their entirety. The MNTF1-F6 gene sequence encodes a 33 amino acid sequence referred to therein as SEQ ID NO:4. Nucleotide sequences encoding MNTF1 polypeptides were found to map within human chromosome 16q22, as described in International Application No. PCT/US2004/038651, which is hereby incorporated by reference in its entirety.

Two overlapping domains within the MNTF1-F6 molecule that appear to be sufficient for the known biological activities of MTF1 were identified. See, International Application No. PCT/US04/01468 or U.S. patent application Ser. No. 10/541,343, which are hereby incorporated by reference in their entirety. Each of these domains, designated herein as the "WMLSAFS" and "FSRYAR" domains, were sufficient to stimulate the proliferation of motor neuron derived cell lines in a manner similar to the MNTF1-F6 33-mer. Similarly, the "PSRYAR" domain is sufficient to direct selective reinnervation of muscle targets by motor neurons in vivo in a manner similar to the MNTF1-F6 33-mer. In addition, the "PSRYAR" domain provides an antigenic epitope sufficient to raise antibody that recognizes any MNTF peptide containing the "FSRYAR" sequence, including the MNTF1-F6 33-mer.

Motoneuron Trophic Factor (MNTF) peaks in expression during week 9 in human fetus gestation period (Di, X. et al., Acta Anatomica Sinica 29:86-89, 1998). Based on the expression of MNTF in the developing human, we reasoned that MNTF may promote the differentiation and/or survival of motoneurons. To examine this, we defined whether MNTF modulates the differentiation of pluripotent embryonic stem cells into motoneurons and enhances the survival of ES cell-derived motoneurons.

As disclosed herein, the inventors have determined that the exposure of ES cells to RA and MNTF analogs directs these cells to generate motor neurons.

II. Methods of Use

MNTF and truncated MNTF molecules, included but not limited to those comprising the YLSAFSRYAR domain, referred to herein as a motor neuron differentiation factors (MDNF), are demonstrated herein to induce differentiation of stem cells or partially differentiated neuronal cells into motor neurons. Such agents provide a novel method for generating and/or isolating a population of motor neurons from stem cell cultures.

The method of the present invention comprises contacting an embryonic stem cell with retinoic acid (RA) and a motor neuron differentiation factor (MNDF). In a preferred embodiment of the present invention, the embryonic stem cell is contacted with RA concomitantly with the motor neuron differentiation factor. Alternatively, the method comprises contacting a partially differentiated neuronal cell with a motor neuron differentiation factor. The factors are provided in amounts effective to produce a differentiated neural cell. These amounts may be readily determined by the skilled artisan, based upon known procedures and methods disclosed herein.

MNTF1 and/or its peptide analogues also promote the survival of mammalian motor neurons in vitro. Accordingly, the present invention provides for the use of an MNTF peptide analogue as a growth factor/supplement for neuronal cell cultures, including a method for promoting the survival of stem cell derived neuronal cell lines, by cultivating stem cell derived neuronal cells in vitro with an effective amount of a MNTF peptide analogue.

The inventors have also discovered that neurons cultured in the presence of neurotrophic factors survive and elaborate processes. Accordingly, in another embodiment, the method of the present invention comprises the step of contacting the stem cell derived motor neurons with at least one MNTF peptide analogue, e.g., following contact with RA and a motor neuron differentiation factor, such as a MNTF peptide analogue as described herein or, alternatively Sonic Hedgehog (Shh), which includes a Shh agonist.

The differentiated motor neurons be isolated or enriched, e.g. by FACS sorting. For example the use of a GFP-based motor neuron marking method permits the characterization of pure populations of ES-cell-derived motor neurons. We have employed this protocol for isolating pure motoneuron population of cells from a mixed population of cells from embryoid bodies. Embryoid bodies are disaggregated to single cells using collagenase and dispase. These single cells are then FACS sorted for GFP, since cells expressing GFP controlled by an HB9 promoter are the true motoneurons in the population.

Accordingly, another aspect of the present invention is directed to a method for isolating and/or purifying a population of differentiated neural cells by: (a) obtaining or generating a culture of embryonic stem cells that express enhanced green fluorescent protein (eGFP) under the control of a motor neuron specific promoter; (b) contacting the culture of embryonic stem cells with an amount of a RA and MNTF effective to produce differentiated neural cells that express eGFP; (d) detecting expression of eGFP in the differentiated neural cells; and (f) isolating the differentiated neural cells that express eGFP.

The inventors have discovered that MNTF and certain MNTF analogues are useful for treating neuronal disorder by virtue of their ability to promote the survival, growth, proliferation, and/or maintenance of mammalian neurons. The inventors have further discovered that, according to certain embodiments, a MNTF peptide or a MNTF analogue modulates a signal transduction pathway that is independent of the sonic hedgehog pathway (e.g. partially or completely independent, depending on the embodiment). Likewise, the inventors have discovered that MNTF peptides and MNTF analogues modulate certain protein kinase pathways, including the expression or activity of certain tyrosine kinases and growth factor receptors. The signal transduction or protein kinase pathways that are regulated include, for example, sonic hedgehog independent pathways.

Sonic Hedgehog (Shh) is a key component responsible for the ventralization of caudalized neurons, acting via its transmembrane receptor components patched-smoothened. The data presented herein shows that MNTF peptides effectively substitute for sonic hedgehog in the differentiation of murine ES cells in vitro into motor neurons in the presence of retinoic acid (Example 5). Addition of MNTF to these ES cultures resulted the expression of mature motor neuron transcription factors (HB9 and Islet ½), expression of the mature motor neuron marker choline acetyl transferase (ChAT), and the generation of neurons capable of conducting action potentials. The data also show that MNTF peptides are capable of generating post-mitotic mature motor neurons in the presence of a specific inhibitor of smoothened receptor signaling (cyclopamine-KAAD). While not wishing to be bound to any particular theory or mechanism, the inventors believe that the data show that MNTF signals through an different pathway than Shh or downstream of smoothened. Based upon data presented herein, the inventors have further determined that MNTF peptides act through the signal transduction pathways described herein to promote the survival, growth, proliferation, and/or maintenance of mammalian neurons. Thus, in another aspect of the invention a MNTF factor or MNTF analogue is administered to modulate the expression or activity of certain signal transduction components. Our data further demonstrates that MNTF treatment of ES cells resulted in the auto-phosphorylation of Tyr972 and Tyr 1162/1163 of the Insulin Receptor (IR) (Example 5). These residues are markers of IR activation. Further, co-immunoprecipitation studies showed the association of specific SH2 domains with IR p85 subunit for PI3kinase) as a result of MNTF treatment on the ES cells. Example 5 also shows that blocking the IGF-1R had no effect on the ability of MNTF to generate motor neurons, but blocking IR abolished this ability.

In certain embodiments, a Insulin Receptor substrate protein expression or activity is modulated in response to the administration of a motoneuronotropic factor (MNTF) analogue to a patient or to a target organ, tissue, or cell. Insulin Receptor substrate proteins (IRS-proteins) are the effectors of both Insulin and IGF-initiated signaling. They share PH and PTB domains near their N-termini, and multiple Tyr phosphorylation motifs in their C-terminal regions. Proteins which bind to tyrosine-phosphorylated IRS-proteins include PI3 Kinase p85, GRB2, SHP2, Nck, Crk, and Fyn. IRS-1 appears to be principally involved in IGF-signaling and cytoskeletal growth. IRS-2 appears to be an important mediator of Insulin signaling, as genetic ablation results in type II diabetes. IRS-3 is expressed primarily in adipocytes and is an unusually potent activator of PI3 Kinase. IRS-4 lacks the tyrosine residues which in the other IRS-proteins binds to SHP2.

In certain embodiments, the protein expression or activity of a IGF-1, IGF-II, or receptor of either is modulated in response to the administration of a motoneuronotropic factor (MNTF) analogue to a patient or to a target organ, tissue, or cell. IGF-I and -II signal through the IGF-I Receptor, which is homologous to the Insulin Receptor. The high-affinity IGF-41 Receptor does not play a direct role in signaling, but regulates the concentration of free IGF-II. The IGFs are involved in skeletal growth, and are essential for prevention of apoptosis. Serum levels of free IGFs are kept low by the action of IGF binding proteins (IGFBPs), which sequester the IGFs. Overexpression of IGFBPs may induce apoptosis, presumably by reduction of free IGF; IGFBP levels are also altered in some cancers. The IGF-I Receptor is not as mitogenic as some other growth factor receptors, but its ability to activate the PI3 Kinase pathway, through the Insulin Receptor Substrate (IRS) proteins, is very important for mediating cell survival.

In certain embodiments, a phosphatidylinositol 3-kinase protein expression or activity is modulated in response to the administration of a motoneuronotropic factor (MNTF) analogue to a patient or to a target organ, tissue, or cell. PI3 kinase (phosphatidylinositol 3-kinase) is responsible for phosphorylation of the 3 position of the inositol ring of PI (4,5)P2, to generate PI(3,4,5)P3, a potent second messenger required for survival signaling, and insulin action. PI3 Kinase is a heterodimeric complex composed of an 85 kDa regulatory subunit and a 110 kDa catalytic subunit. Tyrosine phosphorylation of growth factor receptors creates docking sites for binding of p85 (through its SH2 domains) on the receptors; p85 brings with it p110, which is then proximal to its phospho-lipid substrate on the membrane. PI3 Kinase is also activated by Ras, and by the β:γ subunits of heterotrimeric G-proteins. PI3 Kinase is inhibitable by wortmannin, a useful tool for the study of the PI3 Kinase signaling pathway.

In certain embodiments, a Akt kinase protein expression or activity is modulated in response to the administration of a motoneuronotropic factor (MNTF) analogue to a patient or to a target organ, tissue, or cell. Akt is the major known effector of the PI3 kinase pathway. Generation of PIP3 results in the activation of PDK1, which phosphorylates Akt on Thr308, and another kinase (anticipated PDK) which phosphorylates Akt on Ser473. These phosphorylations additively activate Akt Ser/Thr kinase activity, and the use of phosphorylation state-specific antibodies directed against either of these sites can imply Akt activation. Activation of Akt can be measured directly by immunoprecipitation followed by phosphorylation of a known substrate with radiolabeled ATP. Akt phosphorylates Bad on Ser136, resulting in protection from apoptosis. Other substrates of Akt include GLUT4, cardiac PFK2, and GSK3, which is inactivated by this phosphorylation.

In certain embodiments, a Bad kinase protein expression or activity is modulated in response to the administration of a motoneuronotropic factor (MNTF) analogue to a patient or to a target organ, tissue, or cell. Bad, or "Bcl-2 antagonist of cell death" is member of the Bcl-2 family and an important regulator of life versus death. Unphosphorylated Bad dimerizes with Bcl-2 and Bcl-XL, neutralizing their anti-apoptotic activity. Activation of the PI 3-Kinase pathway leads to activation of Akt which phosphorylates Bad on ser-136. MAP Kinase pathways phosphorylate BAD on ser-112 and recently, PKA has been shown to phosphorylate BAD on ser-155. Phosphorylated Bad binds 14-3-3 proteins and perhaps other factors, which sequester Bad from its proapoptotic role. Assays with phosphorylation state-specific antibodies specific to these sites serve as readouts for the activation of the cell survival pathway.

In certain embodiments, a PI(3,4,5)P3-dependent kinase protein expression or activity is modulated in response to the administration of a motoneuronotropic factor (MNTF) analogue to a patient or to a target organ, tissue, or cell. PI(3,4,5)P3-dependent kinase 1 (PDK1) is a Ser/Thr kinase which has a PH domain and is strongly stimulated by PIP3. The best-characterized substrate of PDK1 is Akt, which is phosphorylated by PDK1 on Thr308, contributing to Akt activation. Two isoforms of PDK1 have been identified. PDK1 is also thought to play a role in the activation of p70 S6 Kinase, and is important for signaling from the T-cell Receptor to NFκB during T-cell activation.

In certain embodiments, a Bax protein expression or activity is modulated in response to the administration of a motoneuronotropic factor (MNTF) analogue to a patient or to a target organ, tissue, or cell. The Bax protein, which shares highly conserved domains with Bcl-2, can form ion-conducting channels in the lipid bilayers of mitochondria, which play an essential role in the apoptotic pathway of many cells by releasing apoptogenic proteins into the cytosol. Bax presents an interesting therapeutic target for many diseases involving apoptosis such as cancer or neurodegenerative disorders.

In certain embodiments, a p53 gene product expression or activity is modulated in response to the administration of a motoneuronotropic factor (MNTF) analogue to a patient or to a target organ, tissue, or cell. The p53 gene is mutated in approximately half of all human cancers. Its gene product is involved in the cellular response to cytotoxic stresses, and together with p19ARF, induces expression of p21Cip1, to cause cell cycle arrest. In addition, p53 is able to induce apoptosis, both by transcriptional and non-transcriptional mechanisms. The amino-terminal 83 amino acids of p53 contain the transactivation domain, as well as the region involved in transcription-independent growth suppression. The carboxy-terminal region contains the DNA-binding domain, which is regulated by three phosphorylation events, and potentially by acetylation also.

In certain embodiments, a Nitric Oxide Synthases protein expression or activity is modulated in response to the administration of a motoneuronotropic factor (MNTF) analogue to a patient or to a target organ, tissue, or cell. Nitric Oxide Synthases (NOS) are dimeric, heme-containing enzymes which produce nitric oxide, and contain a c-terminal reductase and an n-terminal oxygenase domain. Three categories of NOS include nNOS/NOS I/NOS1, expressed primarily in neuronal tissue, iNOS/NOS II/NOS2, inducible in macrophages and certain other cells by inflammatory stimuli, and eNOS/NOS III/NOS3, an epithelial form of constitutively expressed NOS. nNOS and eNOS, which are constitutively expressed, require Ca2+ for activity, and are regulated by Ca2+ influx. iNOS is not dependent on Ca2+. Phosphorylation of the different isoforms at a number of sites has varied effects on protein activity; some are inhibitory and some are activating.

In certain embodiments, a Glycogen Synthase Kinase 3 protein expression or activity is modulated in response to the administration of a motoneuronotropic factor (MNTF) analogue to a patient or to a target organ, tissue, or cell. Glycogen Synthase Kinase 3 (GSK) differs from most serine/threonine kinases in that it is active in the absence of the action of signaling pathways. Two isoforms exist, GSK3α and GSK3β. The function of GSK3 is to phosphorylate Glycogen Synthase and thereby inactivate it. Insulin action stimulates the PI3 Kinase pathway, resulting in Akt activation, which phosphorylates and inactivates GSK3. Glycogen Synthase is then rapidly dephosphorylated, and activated. Other GSK3 substrates include Jun (on inhibitory sites), and eIF2B. Phosphorylation of Tau by GSK3 may relate to development of Alzheimer's disease. Phosphorylation state-specific antibodies directed against the Akt site (Ser21) on GSK3 are suitable for surrogate assays of the activation state of the pathway.

In certain embodiments, a Caspase protein expression or activity is modulated in response to the administration of a motoneuronotropic factor (MNTF) analogue to a patient or to a target organ, tissue, or cell. Cysteine aspartyl proteases related to the *C. elegans* CED-3 death protein comprise the caspase family. All are expressed as proenzymes which are activated by proteolysis. With respect to their roles in apoptosis, Caspases can be subdivided into initiator (Caspases 8, 9, 10) and effector (Caspases 3, 6, 7) caspases, depending on whether they are activated by receptor clustering (initiator) or by mitochondrial permeability transition (effector). Effector caspases, most notably Caspase 3, cleave numerous substrates to effect the morphological changes associated with apoptosis. Among Caspase 3 substrates are DFF45/ICAD, which frees up the DNAse subunit of DFF to cause chromatin degradation, as well as gelsolin, PAK2, D4GDI, all of which are involved in cytoskeletal organization, nuclear lamins and PARP. The significance of PARP cleavage is not clear, but it is an excellent marker for caspase activation and the presumption of ongoing apoptosis.

In certain embodiments, a RAS gene product expression or activity is modulated in response to the administration of a motoneuronotropic factor (MNTF) analogue to a patient or to a target organ, tissue, or cell. Ras proteins are small GTP-binding proteins which unlike the heterotrimeric G-proteins contain all GTPase and effector functions within a single polypeptide. At least three isoforms of Ras exist, Ki-Ras, Ha-Ras, and N-Ras, with distinct expression patterns but similar signaling activity. Ras is palmitoylated and farnesylated at the carboxy terminus, anchoring it in the membrane. In resting cells, Ras is loaded with GDP, and is activated subsequent to growth factor stimulation of receptors, which recruit Ras Guanine nucleotide Exchange Factors to the plane of the membrane. Proximity of exchange factors to the Ras proteins causes release of GDP, and its replacement by GTP. In its GTP-bound form, Ras binds several proteins, including Raf, RalGDS, and PI3 Kinase. Inactivation of Ras occurs by GTP hydrolysis, which is greatly accelerated by RasGAP or NF-1, two known Ras GTPase Activating Proteins. It is possible to assay for Ras activation by incubation of lysates with the Ras-binding domain of Raf-1, which selectively binds to Ras:GTP.

III. Stem Cell Cultures

Embryonic stem (ES) cells are cultured cells, derived from the pluripotent inner cell mass of blastocyst stage embryos, that are capable of replicating indefinitely. In general, ES cells have the potential to differentiate into other cells (i.e., they are pluripotent); thus, they may serve as a continuous source of new cells. Embryonic stem cells for use in the present invention may be obtained from any animal, but is preferably obtained from a mammal (e.g., human, domestic animal, or commercial animal). In one embodiment of the present invention, the embryonic stem cell is a murine embryonic stem cell. In another, preferred, embodiment, the embryonic stem cell is obtained from a human.

Suitable methods for culturing mammalian stem cells are known in the art, e.g., as set forth in U.S. patent application Ser. Nos. 10/362,437, 10/789,266, 10/789,308, 10/928,805 and U.S. Pat. No. 6,833,269, which are all incorporated herein in their entirety. Unless explicitly specified otherwise, aspects of the invention can be practiced using stem cells of any vertebrate species (e.g. stem cells from humans; as well as non-human primates, domestic animals, livestock, and other non-human mammals). Included amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells.

In certain embodiments, prototype "primate Pluripotent Stem cells" (pPS cells) are used. pPS cells include pluripotent cells derived from pre-embryonic, embryonic, or fetal tissue at any time after fertilization. Under appropriate conditions, they are capable of producing progeny of several different cell types that are derivatives of the three germinal layers (endoderm, mesoderm, and ectoderm). pPS cells encompass embryonic cells of various types, including human embryonic stem (hES) cells as described by Thomson et al., *Science* 282:1145 (1998); embryonic stem cells from other primates, such as Rhesus stem cells (Thomson et al., *Proc. Natl. Acad. Sci. USA* 92:7844, (1995)), marmoset stem cells (Thomson et al., *Biol. Reprod.* 55:254 (1996) and human embryonic germ (hEG) cells (Shamblott et al., *Proc. Natl. Acad. Sci. USA* 95:13726 (1998)), as well as other types of pluripotent cells known in the art. Any cells of primate origin that are capable of producing progeny that are derivatives of all three germinal layers are included, regardless of whether they were derived from embryonic tissue, fetal tissue, or other sources. The pPS cells are generally not derived from a malignant source, and it is preferred that the cells are karyotypically normal.

pPS cell cultures are described as "undifferentiated" when a substantial proportion of stem cells and their derivatives in the population display morphological characteristics of undifferentiated cells which are readily apparent when compared to differentiated cells of embryo or adult origin. The undifferentiated pPS cells are easily recognized by those skilled in the art, and typically appear in the two dimensions of a microscopic view in colonies of cells with high nuclear/cytoplasmic ratios and prominent nucleoli. It is common for colonies of undifferentiated cells within the population to often be surrounded by neighboring cells that are differentiated.

IV. Differentiated Neural Cells

Suitable methods for culturing progenitor, partially differentiated and fully differentiated neural cells are known in the art, e.g., as set forth in U.S. patent application Ser. Nos. 10/362,437, 10/789,266, 10/789,308, 10/928,805 and U.S. Pat. No. 6,833,269, which are all incorporated herein in their entirety.

Additionally, as used herein, a "neuronal cell", or "neuron", is a conducting or nerve cell of the nervous system that typically consists of a cell body (perikaryon) that contains the nucleus and surrounding cytoplasm; several short, radiating processes (dendrites); and one long process (the axon), which terminates in twig-like branches (telodendrons), and which may have branches (collaterals) projecting along its course. Examples of neurons include motor neurons.

V. Characterization of Differentiated Neural Cells

Differentiation of ES cells into partially- or fully-differentiated neural cells may be detected by known cellular or molecular procedures, and assays and methods disclosed herein. For example, the cell cultures may be probed for a neuronal marker, such as NeuN (neuronal marker) and/or specific motor neuron markers like HB9 or ChAT.

In another embodiment of the present invention, the differentiated neural cell is genetically marked, in that it expresses enhanced green fluorescent protein (eGFP), as described herein. The eGFP genetic marker may be particularly useful in a method for isolating and/or purifying a population of differentiated neural cells, or in a method for monitoring repopulation of a spinal cord.

VI. Retinoic Acid

RA, or vitamin A, is an aldehyde molecule that is believed to be a morphogen. RA is readily available; it may be obtained, for example, from Sigma Chemical Co. (St. Louis, Mo.). Treatment with RA at final concentration of about 0.0.001-1 µM results in efficient differentiation of stem cells to neural progenitors.

VII. MNTF and MNDF Peptides

As those of skill familiar with the art and the present invention will appreciate, sequences comprising the M L S A F S R Y A R 10mer and 33mer provide MNTF peptide analogues for use in selectively differentiating stem cells into motor neurons in vitro and in vivo. The motor neuron differentiation factors of the present invention may be produced synthetically or recombinantly, or isolated from native cells The sequence of amino acid residues in a protein or peptide comprising the MDNF and MNTF peptide analogues of the present invention are designated herein either through the use of their commonly employed three-letter designations or by their single-letter designations. A listing of these three-letter and one-letter designations may be found in textbooks such as Biochemistry, Second Edition, Lehninger, A., Worth Publishers, New York, N.Y. (1975). When the amino acid sequence is listed horizontally, the amino terminus is intended to be on the left end whereas the carboxy terminus is intended to be at the right end.

It will be appreciated by those of skill that the precise chemical structure of peptides comprising the various MDNF and MNTF peptide analogues will vary depending upon a number of factors. For example, a given polypeptide may be obtained as an acidic or basic salt, or in neutral form, since ionizable carboxyl and amino groups are found in the molecule. For the purposes of the invention, then, any form of the peptides comprising the WMLSAFS, FSRYAR or M L S A F S R Y A R domain(s), which retains a biological activity of the MNTF1 33mer peptide, is intended to be within the scope of the present invention.

FIG. 1 illustrates certain preferred embodiments of MNDF and/or MNTF peptides in accordance with the present invention.

A. MNTF1-F6 33-mer

In U.S. Pat. No. 6,309,877, there is provided a polypeptide (referred to therein as SEQ ID NO: 4) having the following amino acid sequence:

LGTFWGDTLNC *WMLSAFSRYAR*CLAEGHDGPTQ    [SEQ ID NO:1]

Recombinant protein containing this sequence reacted with monoclonal antibody to MNTF-1, maintained motoneuron viability, increased neurite outgrowth, reduced motoneuron cell death/apoptosis and supported the growth and "spreading" of motoneurons into giant, active neurons with extended growth cone-containing axons.

Figure 3:
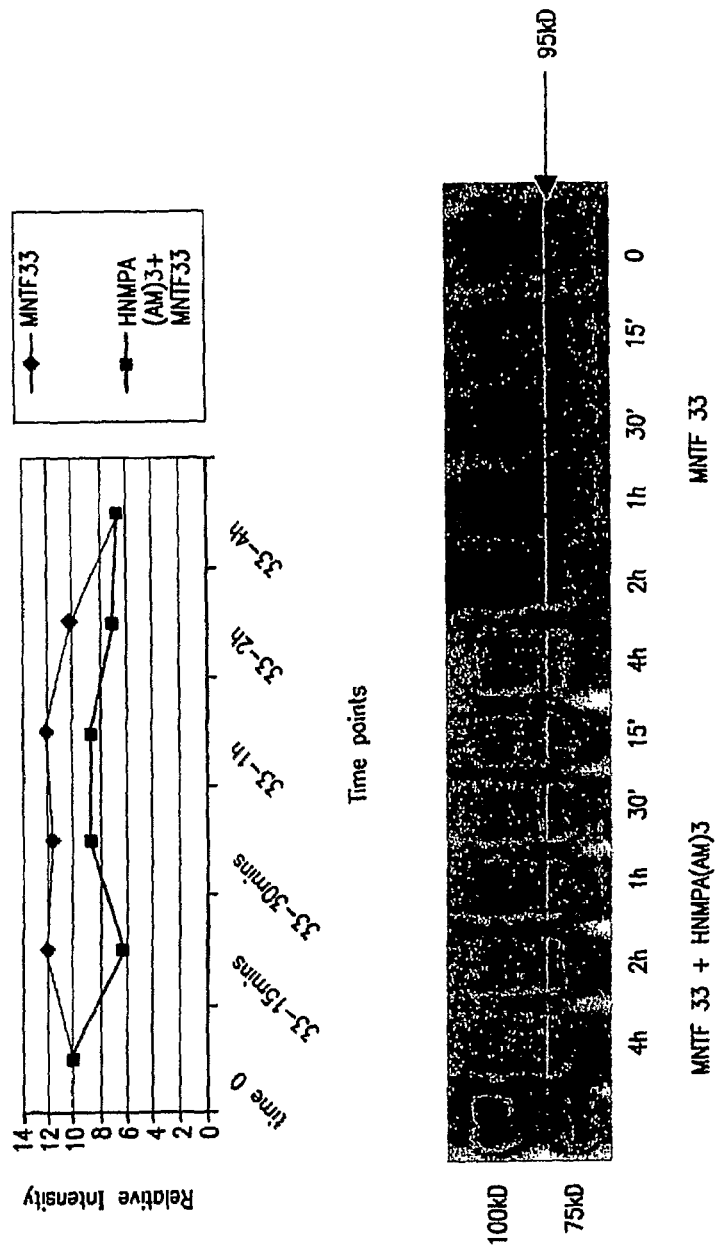
FIG. 3 compares immunoblot results for embryoid bodies treated with MNTF 33mer (MNTF33, (SEQ ID NO:1) or MNTF 33mer and a non-specific inhibitor of insulin receptor (IR) HNMPA(AM)3 using an antibody that detects autophosphorylation of IR or Insulin Growth Factor-1 Receptor (IGF-1R) at pTyr 1162/1163 (3B) which is plotted as relative band intensity (3A)

The MNTF 1 33-mer was synthesized by solid phase synthesis for use in the examples below. This MNTF-1 molecule will be referred to hereinafter as the "33mer." When used in conjunction with a low concentration of RA, the linear 33-mer induced differentiation of ES cells into motor neurons (see FIG. 2). Moreover, MNTF1 induced differentiation of ES cells was not blocked by an inhibitor of the Sonic Hedgehog signal transduction pathway. As shown in FIG. 3, treatment of embryoid bodies with MNTF1 33-mer was associated with autophosphorylation of the insulin receptor (IR) and/or insulin-like growth factor receptor (IGF-R) suggesting MNTF operates through an IR/IGF-R mediated signal transduction pathway.

The present invention includes the use of peptide analogues of MNTF1 that retain the ability of MNTF1 to differentiate stem cells into motor neurons and/or promote the survival and maintenance of stem cell derived motor neurons. An MNTF peptide analogue in accordance with the present invention is typically 6 to 33 amino acids in length and contains at least one of two amino acid sequences, namely the WMLSAFS domain (SEQ ID NO:3) corresponding to amino acid residues 12 to 18 of SEQ ID NO:1, or the FSRYAR domain (SEQ ID NO:2) corresponding to amino acid residues 17 to 22 of SEQ ID NO:1. Preferred embodiments of the MNTF peptide analogue include a fragment of ten to 33 consecutive amino acid residues of SEQ ID NO:1 containing the M L S A F S R Y A R domain (SEQ ID NO:4).

In alternative embodiments the amino acid sequence of the motoneuronotrophic factor peptide analogue is at least 70% identical to nine to 32 consecutive amino acid residues of SEQ ID NO: 1, at least 80% identical to eight to 32 consecutive amino acid residues of SEQ ID NO: 1 and most preferably, a least 90% identical to seven to 32 consecutive amino acid residues of SEQ ID NO: 1 as determined by BLAST analysis.

To compare a polypeptide sequence with the corresponding SEQ ID NO: 1 fragment, a global alignment of the sequences can be performed using the BLAST programs publicly available through the National Center for Biotechnology Information (on the World Wide Web at ncbi.nlm.nih. gov). Prior to performing a global alignment, SEQ ID NO:1 can be submitted to GenBank. Default parameters provided by the National Center for Biotechnology Information can be used for a global alignment.

B. 10-mer

In a particularly preferred embodiment, there is provided a peptide having the following amino acid sequence:

MLSAFSRYAR    [SEQ ID NO:4]

Met Leu Ser Ala Phe Ser Arg Tyr Ala Arg corresponding to amino acid residues 13-22 of the SEQ ID NO:1. This MNTF fragment includes most of the WMLSAFS domain as well as the entire FSRYAR domain. The MNTF 10mer was at least as effective the full-length MNTF 33mer at stimulating differentiation of embryonic stems cells into motor neurons in vitro at concentrations as low as 0.01 µg/ml (see FIG. 2). In addition, the MNTF 10mer was nearly as effective as the MNTF 33mer at enhancing the survival of stem cell derived motor neurons (see FIG. 4). This portion of the MNTF-1 molecule will be referred to hereinafter as the "10 mer"

C. 6-mer

In another embodiment, there is provided a peptide having the following amino acid sequence:

F S R Y A R    [SEQ ID NO:2]

Figure 4:
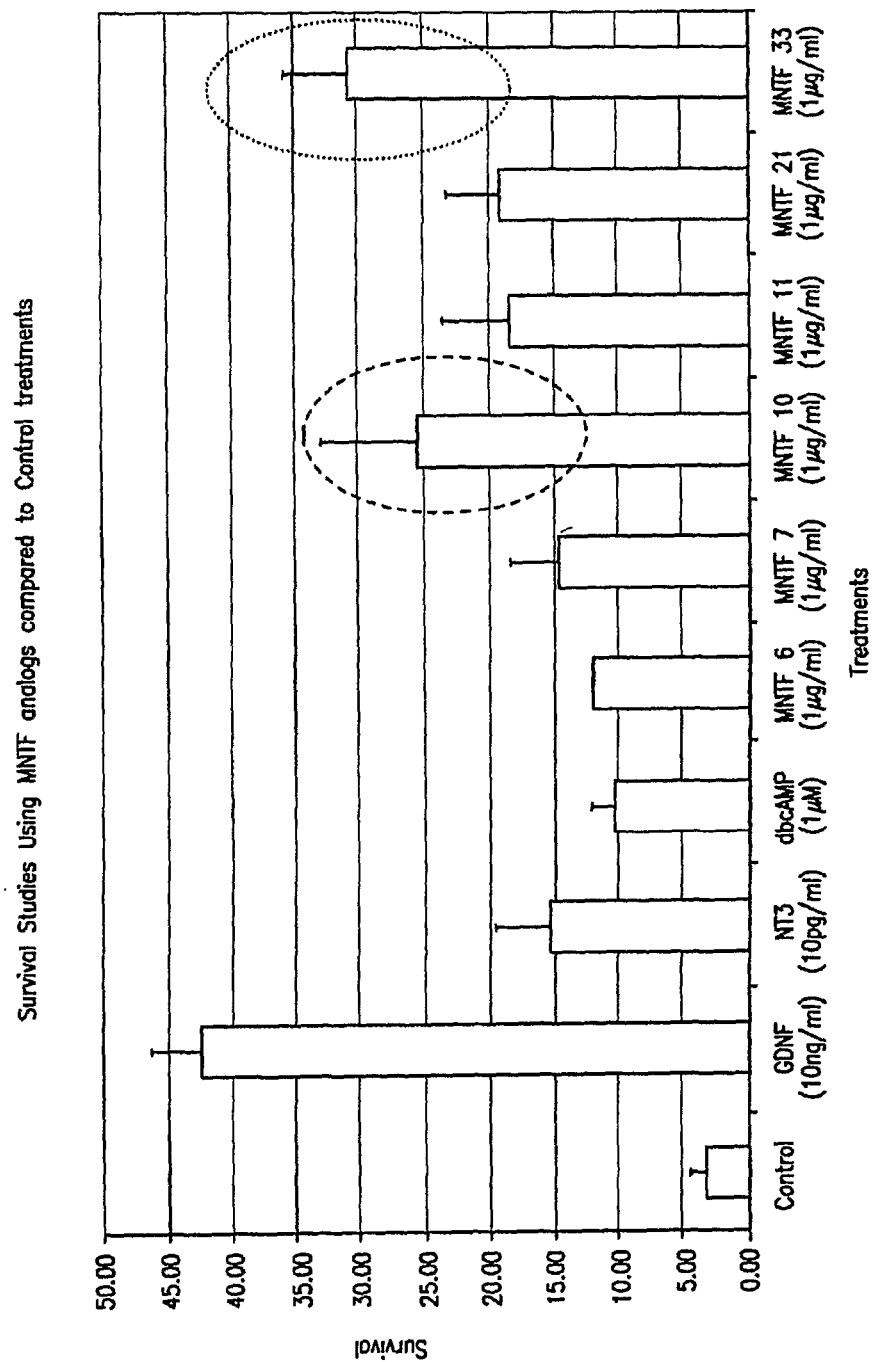
FIG. 4 compares the enhanced survival of ES cell-derived motor neurons treated with GDNF, NT3, dbcAMP or MNTF peptide analogs, wherein percentage survivability is calculated on day ten by counting the total number of cells with existing axons.

Phe-Ser-Arg-Tyr-Ala-Arg corresponding to amino acid residues 17-22 of SEQ ID NO:1, which was found to be sufficient to enhance survival of stem cell derived motor neurons (see FIG. 4). This portion of the MNTF-1 molecule will be referred to hereinafter as the "6mer".

D. 7-mer

In another preferred embodiment, there is provided a peptide having the following amino acid sequence:

W M L S A F S    [SEQ ID NO:3]

Trp Met Leu Ser Ala Phe Ser corresponding to amino acid residues 12-18 of SEQ ID NO:1. This 7 amino acid fragment of MNTF1 overlaps the FS residues of the FSRYAR domain. The peptide was also found to be sufficient to enhance survival of stem cell derived motor neurons (see FIG. 4). This portion of the MNTF-1 molecule will be referred to hereinafter as the "7mer".

E. 11-mer

In another preferred embodiment, there is provided a peptide having the following amino acid sequence:

FSRYARCLAEG    [SEQ ID NO;5]

Phe-Ser-Arg-Tyr-Ala-Arg-Cys-Leu-Ala-Glu-Gly corresponding to amino acid residues 17-27 of SEQ ID NO:1. The MNTF1 11-mer contains the FSRYAR domain and was also found to be sufficient to enhance survival of stem cell derived motor neurons (see FIG. 4). This portion of the MNTF-1 molecule will be referred to hereinafter as the "11mer".

F. 21-mer

In another preferred embodiment, there is provided a peptide having the following amino acid sequence:

```
MLSAFSRYARCLAEGHDGPTQ            [SEQ ID NO:6]
Met Leu Ser Ala Phe Ser Arg Tyr Ala
Arg Cys,Leu Ala Glu Gly His Asp Gly
Pro Thr Gln
``` corresponding to amino acid residues 13 to 33 of SEQ ID NO:1. This MNTF1 21-mer contains most of the "WMLSAFS" domain as well as the entire FSRYAR domain and was also found to be sufficient to enhance survival of stem cell derived motor neurons (see FIG. 4). This portion of the MNTF-1 molecule will be referred to hereinafter as the "21mer".

VIII. MNTF Peptide Analogues

It is to be understood that within the scope of the present invention are peptide analogues as described and identified herein in which one or more amino acids are substituted with other amino acids. In a preferred alternative, the motoneuronotrophic factor peptide analogue contains one or more conservative amino acid substitutions to a fragment of seven to 32 consecutive amino acid residues of SEQ ID NO:1.

An MNTF peptide analogue within the scope of this invention can be an altered form of an MNTF1 peptide providing generally of course that the essential activity of the peptide remains substantially unchanged. As used herein, the term "altered form" refers to a peptide that has been treated to change its naturally occurring structure. An altered form can be prepared, for example, by covalent modification of an MNTF1 peptide fragment, by crosslinking MNTF1 peptide fragment to an insoluble support matrix, or by crosslinking MNTF1 peptide fragment to a carrier protein.

An MNTF1 peptide analogue within the scope of this invention can be a peptide fragment that is antigenically related to an MNTF1 peptide fragment. Two peptides, which are antigenically related display immunological cross-reactivity. For example, antibodies to the first peptide also recognize the second peptide.

An MNTF1 peptide analogue within the scope of this invention can be a fusion protein containing a MNTF1 peptide fragment attached to a heterologous protein. A heterologous protein has an amino acid sequence not substantially similar to the MNTF1 peptide fragment. The heterologous protein can be fused to the N-terminus or C-terminus of the MNTF1 peptide fragment. Fusion proteins can include, but are not limited to, poly-His fusions, MYC-tagged fusions, Ig fusions and enzymatic fusion proteins, for example beta-galactosidase fusions. Such fusion proteins, particularly poly-His fusions, can facilitate the purification of recombinant MNTF1 peptide fragments.

Peptidomimetics of MNTF peptide(s) are also provided by the present invention, and can act as drugs for the modulation of neuronal cell viability and growth by, for example, blocking the function of proteins comprising the WMLSAFS and/or FSRYAR domain(s). Peptidomimetics are commonly understood in the pharmaceutical industry to include non-peptide drugs having properties analogous to those of the mimicked peptide. The principles and practices of peptidomimetic design are known in the art and are described, for example, in Fauchere J., *Adv. Drug Res.* 15: 29 (1986); and Evans et al., *J. Med. Chem.* 30: 1229 (1987).

Peptidomimetics which bear structural similarity to therapeutically useful peptides may be used to produce an equivalent therapeutic or prophylactic effect. Typically, such peptidomimetics have one or more peptide linkages optionally replaced by a linkage, which may convert desirable properties such as resistance to chemical breakdown in vivo. Such linkages may include —$CH_2NH$—, —$CH_2S$—, —$CH_2$—$CH_2$—, —CH=CH—, —$COCH_2$—, —$CH(OH)CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

The rational design of WMLSAFS and/or FSRYAR domain mimetics or binding molecules, based on modeled (or experimentally determined) peptide structure, may be carried out by those of skill, using known methods of rational drug design. The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

IX. Methods of Making

It is understood that an MNTF peptide composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an MNTF peptide of the present invention in an in vitro translation system or in a living cell. Preferably the MNTF peptide of the composition is isolated and extensively dialyzed to remove one or more undesired small molecular weight molecules and/or lyophilized for more ready formulation into a desired vehicle. It is further understood that additional amino acids, mutations, chemical modification and such like, if any, that are made in a MNTF peptide component will preferably not substantially interfere with receptor recognition of the MNTF docking sequence.

A peptide or polypeptide corresponding to one or more fragments of MNTF1 of the present invention should generally be at least five or six amino acid residues in length, and may contain up to about 7, about 8, about 9, about 10, about 11, about 12, about 13, about 15, about 20 or about 30 residues or so. A peptide sequence may be synthesized by methods known to those of ordinary skill in the art, such as, for example, peptide synthesis using automated peptide synthesis machines, such as those available from Applied Biosystems (Foster City, Calif.). The invention further provides the synthesis and use of cyclic peptides such as those derived from (SEQ ID NO:1) and (SEQ ID NO:6) as shown in Table 1 below.

Covalent modifications can be introduced into a peptide by reacting targeted amino acid residues with an organic derivatizing agent that is capable of reacting with selected side chains or terminal residues. Covalent modification of polypeptides using organic derivatizing agents is well known to those of skill in the art. For example, cysteinyl residues can be reacted with α-haloacetates (and corresponding amines), such as chloroacetic acid or chloroacetamide, to give carboxymethyl or carboxyamidomethyl derivatives. Histidyl residues can be derivatized by reaction with diethylpyrocarbonate at pH 5.5-7.0, or with para-bromophenacyl bromide at pH 6 in 1 M sodium cacodylate. Lysinyl and amino terminal residues can be reacted with succinic or other carboxylic acid anhydrides. Arginyl residues can be modified by reaction with one or several conventional reagents, among them phenylglyoxal, 2,3-butanedione, 1,2-cyclohexanedione, and ninhydrin. Spectral labels can be introduced into tyrosyl residues by reaction with aromatic diazonium compounds or tetranitromethane; most commonly, N-acetylimidizol and tetranitromethane are used to form 0-acetyl tyrosyl species and 3-nitro derivatives, respectively. Carboxyl side groups (aspartyl or glutamyl) can be selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues can be deamidated to the corresponding glutamyl and aspartyl residues. Other modifications include hydroxylation of proline and lysine, phosphorylation of hydroxyl groups of seryl or threonyl residues, methylation of the α-amino groups of lysine, arginine, and histidine side chains (T. E. Creighton, 1983, Proteins: Structure and Molecule Properties, W.H. Freeman & Co., San Francisco, pp. 79-86), acetylation of the N-terminal amine, and, in some instances, amidation of the C-terminal carboxyl groups.

The invention further provides the MNTF peptide analogues for use in assays and kits for assays, either in the free form or linked to a carrier molecule such as a protein or a solid particle, as well as modified peptides linked to a label or tracer e.g. biotin or fluorescein isothiocyanate.

Crosslinking of MNTF1 peptide fragment to a water-insoluble support matrix can be performed with bifunctional agents well known in the art including 1,1 bis(diazoacetyl) 2 phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Bifunctional agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates can be employed for protein immobilization.

Crosslinking of an MNTF1 peptide fragment to a second protein, including a second MNTF1 peptide fragment, can be performed using the bifunctional reagents described herein. In another alternative, there is inserted a spacer, for example a dithiol group or a diamino group or multiples of amino acid residues, e.g. glycine. The spacer may also be a homo- or hetero-bifunctional crosslinker, for example the heterobifunctional crosslinker N-(4-carboxy-cyclohexyl-methyl)-maleimide.

Longer peptides or polypeptides, e.g a fusion protein, can be produced by standard recombinant DNA techniques. For example, a DNA fragment encoding a MNTF1 peptide fragment can be cloned in a commercially available expression vector that already contains a heterologous protein, with the result being MNTF1 peptide fragment fused in-frame to the heterologous protein.

In certain embodiments, a nucleic acid encoding an MNTF1 peptide and/or a component described herein may be used, for example, to produce a peptide in vitro or in vivo for the various compositions and methods of the present invention. For example, in certain embodiments, a nucleic acid encoding an MNTF1 peptide is a component of, for example, a vector in a recombinant cell. The nucleic acid may be expressed to produce a peptide or polypeptide comprising an MNTF1 peptide sequence. The peptide or polypeptide may be secreted from the cell, or as part of or within the cell.

X. Compound Screening

In another embodiment, compounds which alter the level of expression of a MNTF peptide or a protein involved in the intracellular signal transduction pathway of a MNTF peptide are identified. In certain embodiments, these compound are targeted for the treatment of various neural disorders described herein.

Agonist and antagonists of neuroprotection can be distinguished, and the efficacy of the compound can be assessed, by subsequent testing with neuronal cells described herein and known in the art.

Compounds identified by the screening procedures described herein can further be distinguished, and the efficacy of the compound can be assessed, based upon their ability to treat neuronal disorders in art accepted animal cell culture disease and disorder model systems, including described in co-pending application U.S. Ser. No. (to be assigned), filed Nov. 10, 2006, entitled "Methods of Treating Neuronal Disorders using MNTF peptides and analogues thereof" incorporated by reference herein in its entirety.

In many drug screening assays which test libraries of compounds and natural extracts, high throughput assays are desirable in order to maximize the number of compounds surveyed in a given period of time. Assays which are performed in cell-free systems, such as may be derived with purified or partially purified proteins, are often preferred as "primary" screens in that they can be generated to permit rapid development and relatively easy detection of an alteration in a molecular target which is mediated by a test compound. Further, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Thus in another aspect, a method of identifying a compound useful for promoting the growth or survival of motoneurons is provided. In one embodiment, the method comprises the steps of i) preparing a sample comprising a candidate compound, ii) contacting a cell with said sample, iii) determining whether the expression or activity of a compound involved in signal transduction pathway is modulated, and iv) determining whether the sample is capable of promoting the growth or survival of motorneurons. In certain embodiments, the method further comprises determining whether a sample containing a candidate compound stimulates the autophosphorylation of Tyr972 and Tyr1162/1163 of the insulin receptor in vitro or in vivo. In other embodiments, the method further comprises determining whether a sample containing a candidate compound regulates a MNTF signal transduction pathway. In other embodiments, the method further comprises determining whether a sample containing a candidate compound modulates the expression or activity of one or more proteins selected from a insulin receptor, IGF-1 receptor, IGF-2 receptor, Shh, Akt, Bad (bcl-2 antagonist of cell death), PI(3,4,5)P3-dependent kinase 1 (PDK1), Bax, p53 gene product, pp60-Src, JAK2, nitric oxide synthases (NOS), glycogen synthase kinase 3 (GSK), caspase, PI3 kinase (phosphatidylinositol 3-kinase), and Ras. In other embodiments, the method further comprises determining whether a sample containing a candidate compound is regulated by a MNTF analogue, or alternatively regulated a MNTF analogue (e.g. activity, expression, etc.). In another aspect, the invention provides methods of promoting the growth or survival of a motoneuron or for the treatment of a neuronal disorder by administering a compound identified by the screening procedures described herein.

In an exemplary screening assay, the compound of interest is contacted with a mixture including a MNTF binding protein (e.g., a cell expressing a MNTF peptide receptor) and a MNTF peptide under conditions in which it is ordinarily capable of binding a MNTF peptide. To the mixture is then added a composition containing a test compound. Detection and quantification of receptor/MNTF peptide complexes provides a means for determining the test compound's efficacy at inhibiting (or potentiating) complex formation between the receptor protein and the MNTF peptide. A control assay can also be performed to provide a baseline for comparison, in which isolated and purified MNTF peptide is added to the receptor protein and the formation of receptor/MNTF peptide complex is quantitated in the absence of the test compound.

Complex formation between the MNTF peptide and a MNTF peptide may be detected by a variety of techniques. For instance, modulation of the formation of complexes can be quantitated using, for example, detectably labelled proteins such as radiolabelled, fluorescently labelled, or enzymatically labelled MNTF peptides, by immunoassay, or by chromatographic detection. For cell-free assays, it will typically be desirable to immobilize either the MNTF peptide or the MNTF peptide binding protein to facilitate separation of receptor/MNTF peptide complexes from uncomplexed forms of one of the proteins, as well as to accommodate automation of the assay. For example, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the MNTF peptide, e.g., an $^{35}$S-labeled MNTF peptide, and the test compound and incubated under conditions conducive to complex formation, e.g., at physiological conditions for salt and pH, though slightly more stringent conditions may be desired. Following incubation, the beads are washed to remove any unbound MNTF peptide, and the matrix bead-bound radiolabel determined directly (e.g., beads placed in scintillant), or in the supernatant after the receptor/hedgehog complexes are dissociated. Alternatively, the complexes can be dissociated from the bead, separated by SDS-PAGE gel, and the level of MNTF peptide found in the bead fraction quantitated from the gel using standard electrophoretic techniques.

Other techniques for immobilizing proteins on matrices are also available for use in the subject assay. For instance, soluble portions of the MNTF peptide protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the MNTF peptide but which do not interfere with hedgehog binding can be derivatized to the wells of the plate, and the receptor trapped in the wells by antibody conjugation. As above, preparations of a MNTF peptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the MNTF peptide, or which are reactive with the receptor protein and compete for binding with the MNTF peptide; as well as enzyme-linked assays which rely on detecting an enzymatic activity associated with the MNTF peptide. In the instance of the latter, the enzyme can be chemically conjugated or provided as a fusion protein with the MNTF peptide. To illustrate, the MNTF peptide can be chemically cross-linked or genetically fused with alkaline phosphatase, and the amount of MNTF peptide trapped in the complex can be assessed with a chromogenic substrate of the enzyme, e.g., paranitrophenylphosphate. Likewise, a fusion protein comprising the MNTF peptide and glutathione-S-transferase can be provided, and complex formation quantitated by detecting the GST activity using 1-chloro-2,4-dinitrobenzene (Habig et al., *J Biol Chem,* 249:7130 (1974)). For immunodetection for quantitating one of the proteins trapped in the complex, antibodies against the protein, such as the anti-MNTF peptide antibodies can be used. Alternatively, the protein to be detected in the complex can be "epitope tagged" in the form of a fusion protein which includes, in addition to the MNTF peptide or MNTF peptide sequence, a second polypeptide for which antibodies are readily available (e.g., from commercial sources). For instance, the GST fusion proteins described above can also be used for quantification of binding using antibodies against the GST moiety. Other useful epitope tags include myc-epitopes (e.g., see Ellison et al., *J Biol Chem* 266:21150-21157 (1991)) which includes a 10-residue sequence from c-myc, as well as the pFLAG system (International Biotechnologies, Inc.) or the pEZZ-protein A system (Pharamacia, N.J.).

XI. Compositions

Pharmaceutical compositions for use in accordance with the present invention preferably comprise one or more of the MNTF peptide analogues of the present invention together with a pharmaceutically acceptable diluent and/or carrier. Suitable carriers/diluents are well known in the art and include saline or other sterile aqueous media, optionally including additional components such as buffer salts and preservatives, or sugars, starches, salts or mixtures thereof.

Compositions containing MNTF peptides according to the present invention may be provided for use in any suitable form appropriate to the protocol of administration and/or the needs of a patient. For example, with respect to the present invention, the active ingredient(s) may be applied in vitro prior to transplantation or in vivo internally at or near the site of transplanted stem cells or their derivatives.

The invention further provides culture media that are useful for establishing and propagating stem cells, neural progenitor cells, differentiated neural cells and stem-cell derived motor neurons. The media are particularly suitable for the differentiation of stem cells and long-term culture of stem cell derived motor neurons.

The cell culture media of this invention are desirably supplemented with morphogens and/or growth factors, and optimized according to the individual cell type desired to be cultured. Such supplementation and optimization are within the ordinary skill in the art. In some preferred embodiments, the invention is a cell culture medium that may be supplemented with any or all of the following morphogens and/or growth factors at the following approximate levels (or within one significant digit): RA at 0.001-1 µM, Shh or Shh agonist, at 0.001-1 µM, and/or one or more MNTF peptide analogues at 0.01-250 µg/ml.

The pharmaceutical formulations of the present invention may include, as optional ingredients, pharmaceutically acceptable carriers, diluents, solubilizing or emulsifying agents, and salts of the type that are available in the art.

Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0. Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation.

Compounds provided herein may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the peptide.

Pharmaceutical compositions are generally formulated for administered for a therapeutic purpose. Pharmaceutical compositions may also include one or more active ingredients such as interferons, antimicrobial agents, anti-inflammatory agents, anesthetics, and the like. Formulations for parenteral administration may include sterile aqueous solutions which may also contain buffers, liposomes, diluents and other suitable additives. Pharmaceutical compositions comprising the peptides provided herein may include penetration enhancers in order to enhance the alimentary delivery of the peptides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 8, 91-192 (1991); Muranishi, Critical Reviews in Therapeutic Drug Carrier Systems 7, 1-33 (1990)). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Lee et al., Critical Reviews in Therapeutic Drug Carrier Systems page 92 (1991); Muranishi, Critical Reviews in Therapeutic Drug Carrier Systems 7, 1 (1990); El-Hariri et al., J. Pharm. Pharmacol. 44, 651-654 (1992)).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al. McGraw-Hill, New York, N.Y., pages 934-935 (1996)). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems page 92 (1991); Muranishi, Critical Reviews in Therapeutic Drug Carrier Systems 7, 1-33 (1990); Buur et al., J. Control Rel. 14, 43-51 (1990)). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems page 92 (1991)); and perfluorochemical emulsions, such as FC-43 (Takahashi et al., J. Pharm. Pharmacol. 40, 252-257 (1988)). Non-surfactants include, for example, unsaturated cyclic ureas, 1-alkyl- and 1-alkenylazacyclo-alkanone derivatives (Lee et al., Critical Reviews in Therapeutic Drug Carrier Systems page 92 (1991)); and non-steroidal anti-inflammatory agents such as diclofenac sodium, indomethacin and phenylbutazone (Yamashita et al., J. Pharm. Pharmacol. 39, 621-626 (1987)).

Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions provided herein.

Regardless of the method by which compounds are introduced into a patient, colloidal dispersion systems may be used as delivery vehicles to enhance the in vivo stability of the peptides and/or to target the peptides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:peptide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 6, 698-708 (1995)).

In certain embodiments, MNTF peptides and MNTF analogues can be incorporated into or used in conjunction with a biodistribution directing moiety, including one or more polymer, to direct the biodistribution of the MNTF peptide or MNTF analogue or other compound provided herein to the proximity of the a desired target or to allow for continuous release of thereof. Active agents include, for example, compounds useful for increasing therapeutic efficacy, for optimizing biodistribution and bioavailability, for reducing tissue damage, for promoting healing, or for increasing patient comfort; exemplary active agents include vasoactive agents, anesthetics, therapeutic agents for ischemia, growth factors and cytokines. Alternatively, microparticulate or nanoparticulate polymeric bead dosage forms may be used in composition provided herein. Compounds provided herein may be used in combination with an active agent and encapsulated in a particulate dosage form with a number of ligand or anti-ligand molecules attached thereto.

In this manner, MNTF peptides and MNTF analogues, and other compounds provided here, alone or in combination with other active agents, are released at that site over time to provide a sustained therapeutic benefit. Sustained release dosage forms are also useful with regard to other active agents useful in the practice of the present invention, such as growth factors, cytokines, and the like. Release of the active agent from the particulate dosage forms of the present invention can occur as a result of both diffusion and particulate matrix erosion. Biodegradation rate directly impacts active agent release kinetics.

In certain embodiments, controlled release parenteral formulations of MNTF peptides, MNTF analogues, and compounds of the present invention can be made as implants, oily injections, or as particulate systems. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Liposomes can be used for controlled release as well as drug targeting of entrapped drug.

In certain embodiments, the pharmaceutical composition of the invention, including MNTF peptides and MNTF analogues, can be administered locally, topically, nasally, orally, gastrointestinally, intrabronchially, intravesically, intravaginally, into the uterus, sub-cutaneously, intramuscularly, periarticularly, intraarticularly, into the cerebrospinal fluid (ICSF), into the brain tissue (e.g. intracranial administration), into the spinal medulla, into wounds, intraperitoneally or intrapleurally, or systemically, e.g. intravenously, intraarterially, intraportally or into the organ directly.

A variety of catheters and delivery routes can be used to achieve intracoronary delivery, as is known in the art. For example, a variety of general-purpose catheters, as well as modified catheters, suitable for use in the present invention are available from commercial suppliers such as Advanced Cardiovascular Systems (ACS), Target Therapeutics and Cordis. Also, where delivery to the myocardium is achieved by injection directly into a coronary artery (which is presently most preferred), a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery.

Detailed descriptions of these and other techniques can be found in the art (see, e.g., Topol, E J (ed.), The Textbook of Interventional Cardiology, 2nd Ed. (W.B. Saunders Co. 1994); Rutherford, R B, Vascular Surgery, 3rd Ed. (W.B. Saunders Co. 1989); Wyngaarden J B et al. (eds.), The Cecil Textbook of Medicine, 19th Ed. (W. B. Saunders, 1992); and Sabiston, D, The Textbook of Surgery, 14th Ed. (W.B. Saunders Co. 1991)).

The compounds provided herein may be administered parentally. It is sometimes preferred that certain compounds are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intracerebral, intravenous, subcutaneous, or transdermal administration. The formulation which is administered may contain such agents. Example of these agents include cationic agents (for example calcium phosphate and DEAE-dextran) and lipofectants (for example Lipofectam™ and Transfectam™).

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated gloves, condoms, and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral administration may include sterile aqueous solutions which may also contain buffers, diluents and other suitable additives. In some cases it may be more effective to treat a patient with an peptide in conjunction with other traditional therapeutic modalities in order to increase the efficacy of a treatment regimen. As used herein, the term "treatment regimen" is meant to encompass therapeutic, palliative and prophylactic modalities.

Dosing can be dependent on a number of factors, including severity and responsiveness of the disease state to be treated, and with the course of treatment lasting from several days to several months, or until a cure is effected or a diminution of the disease state is achieved. Toxicity and therapeutic efficacy of compounds provided herein can be determined by standard pharmaceutical procedures in cell cultures or experimental animals. For example, for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Dosing schedules can be calculated from measurements of drug accumulation in the body of the patient. Dosages may vary depending on the relative potency of individual compounds, including MNTF peptides and MNTF analogues, and can generally be estimated based on EC50s found to be effective in vitro and in in vivo animal models. One of skill in the art will recognize that preferred dosages will vary depending on how and where an MNTF peptide is administered (e.g. in vitro, in vivo, topically, systemically, etc.).

For example, in one aspect, MNTF peptides and MNTF analogues may be administered to achieve from about 0.01 micrograms per ml (µg/mL) to about 1 mg per ml, from about 0.1 µg/mL to about 50 µg/mL, from about 0.1 µg/mL to about 150 µg/mL, from about 1 µg/mL to about 200 µg/mL, and from about 0.1 µg/mL to about 500 µg/mL, including any range within these ranges, final concentrations at a target site (e.g. in a cell culture of ES stem cells).

Alternative suitable dosage amounts may, for example, vary from about 0.1 ug up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides, polypeptides, and compounds provided herein will be specific to particular cells, conditions, and locations. In general, dosage generally ranges from 0.01 mg/kg to 1000 mg per kg of body weight, and more typically, for example, from 0.1 mg/kg to 300 mg per kg of body weight, and may be given once or more daily, weekly, monthly or yearly, or even once or more during a time span of 2 to 20 years. In certain embodiments, the dosage may be given from immediately post surgery to 24 hours, in another embodiment; the dosage is given from 2 hours and up to 24 hours. Long-acting compositions may be administered every 3 to 4 days, every week, or biweekly depending on the half-life and clearance rate of the particular formulation. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein a selected compound is administered in maintenance doses, ranging from 0.01 mg/kg to 100 mg per kg of body weight, once or more daily, to once every 20 years. In the treatment or prevention of certain conditions, an appropriate dosage level will generally be about 0.001 to 100 mg per kg patient body weight per day which can be administered in single or multiple doses. A suitable dosage level can be about 1 to about 40 mg/kg per day. In certain embodiments, compounds provided herein, including MNTF peptides and MNTF peptide analogues, are administered in an amount to achieve in vivo concentrations from about 1 micromolar to about 1 millimolar, from about 10 micromolar to about 500 micromolar, or from about 30 micromolar to about 300 micromolar, and from about 25 micromolar to about 300 micromolar final concentration over the damaged site, and including, about 25 micromolar, or about 160 micromolar, or about 300 micromolar final concentration over the damaged site, and still more typically between about 1 micromolar to about 100 micromolar.

Compounds described herein can be used in diagnostics, therapeutics, prophylaxis, and as research reagents and in kits. Provision of means for detecting compounds of interest (e.g. MNTF peptides and MNTF analogues) can routinely be accomplished. Such provision may include enzyme conjugation, radiolabelling or any other suitable detection systems. Kits for detecting the presence or absence of compounds of interest may also be prepared.

The compounds of the invention may also be used for research purposes. Thus, the specific hybridization exhibited by the peptides may be used for assays, purifications, cellular product preparations and in other methodologies which may be appreciated by persons of ordinary skill in the art.

Technical and scientific terms used herein have meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., Molecular Cloning: A Laboratory Manual, 2d Ed., Cold Spring Harbor Laboratory Press, Planview, N.Y. (1989) and Molecular Cloning: A Laboratory Manual, third edition (Sambrook and Russel, 2001), jointly and individually referred to herein as "Sambrook"; McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlagsgesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. (jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993); Teratocarcinomas and embryonic stem cells: A practical approach (E. J. Robertson, ed., IRL Press Ltd. (1987); Guide to Techniques in Mouse Development (P. M. Wasserman et al. eds., Academic Press (1993); Embryonic Stem Cell Differentiation in vitro (M. V. Wiles, *Meth. Enzymol.* 225:900 (1993); Properties and uses of Embryonic Stem Cells: Prospects for Application to Human Biology and Gene Therapy (P. D. Rathjen et al., *Reprod. Fertil. Dev.,* 10:31 (1998)); CNS Regeneration: Basic Science and Clinical Advances, M. H. Tuszynski & J. H. Kordower, eds., Academic Press, (1999). Certain techniques that may be useful in the practice of the invention are described in various patents and patent applications, including U.S. Pat. No. 5,851,832, which reports multipotent neural stem cells obtained from brain tissue, U.S. Pat. No. 5,766,948 which reports producing neuroblasts from newborn cerebral hemispheres, U.S. Pat. Nos. 5,654,183 and 5,849,553 which report the use of mammalian neural crest stem cells, U.S. Pat. No. 6,040,180 which reports in vitro generation of differentiated neurons from cultures of mammalian multipotential CNS stem cells, WO 98/50526 and WO 99/01159 which report generation and isolation of neuroepithelial stem cells, oligodendrocyte-astrocyte precursors, and lineage-restricted neuronal precursors, and U.S. Pat. No. 5,968,829 which reports neural stem cells obtained from embryonic forebrain and cultured with a medium comprising glucose, transferrin, insulin, selenium, progesterone, and several other growth factors.

Any suitable materials and/or methods known to those of skill can be utilized in carrying out the present invention; however, non-limiting preferred materials and/or methods are described herein.

The invention may be appreciated in certain aspects with reference to the following examples, offered by way of illustration, not by way of limitation. Materials, reagents and the like to which reference is made in the following examples are obtainable from commercial sources, unless otherwise noted.

EXAMPLE 1

Differentiation of ES Cells into Motor Neurons

A. Materials and Methods
 1. Embryonic Stem (ES) Cell Cultures
 ES cells were derived from an HB9-GFP-transgenic mouse and fluoresce green upon adoption of a motoneuron phenotype [Wichterle, H. et al. (2000) Cell 110, 385-397, incorporated herein by reference]. The mouse ES cells were maintained in a proliferative and undifferentiated state in the presence of murine LIF (Chemicon). The ES cells were cultured on a feeder layer of primary mouse embryonic fibroblasts that were mitomycin treated.
 2. Materials
 Retinoic Acid (RA) was obtained from Sigma (R-2625). Sonic hedgehog (Shh) agonist, Hh-Ag1.3, was obtained from Curis, Inc. (Cambridge, Mass.). MNTF 6-mer, 7-mer, 10-mer, 11-mer, 21-mer, and 33-mer peptides were obtained by from CS Bio Company (Menlo Park, Calif.), who produced the peptides by solid phase synthesis in accordance with amino acid sequence information provided by Genervon Biopharmaceuticals LLC (Montebello, Calif.).
 3. Differentiation Protocol
 Mouse ES cells were separated from the feeder layer of fibroblasts. This was done by trypsinizing and plating the cell mixture on cell culture flasks coated with 0.1% gelatin. The fibroblasts attached specifically on the gelatin leaving a pure population of floating ES cells. The floating ES cells were collected and resuspended in differentiating medium. This stage was called "d−1". The ES cells formed embryoid bodies (EBs) and 24 hours later ("d0") were exposed to RA (1 μM)+MNTF or RA (1 μM)+Shh agonist (1 μM). MNTF peptides (all six forms) were tested at a final concentration range of 0.1 μg/ml-150 μg/ml.
 The differentiation assay was carried for six days from "d−1" stage.
B. Results
 The photo micrographs in FIG. 2 show expression of eGFP under the control of the HB9 promoter. HB9 expression is a marker for fully differentiated motor neurons. As shown in FIG. 2, EBs treated with RA and either MNTF 10-mer or 33-mer expressed eGFP and fluoresced green to the same extent or greater than EBs treated with RA and Shh agonist. Our data shows that the MNTF 10-mer and 33-mer peptide provided herein were successful in the differentiation process. Elevated fluorescence was detectable at concentrations of MNTF 10-mer or 33mer as low as 0.1 g/ml and, in this experiment, appeared to be optimal at about 10 μg/ml.
C. Conclusions
 MNTF 10-mer and 33-mer are capable of inducing differentiation of ES cells into differentiated motor neurons in the presence of low concentrations of RA. These findings suggest treatment of ES, neural progenitor or partially-differentiated neural cells with MNTF 10-mer or 33-mer in vitro or in vivo can steer differentiation of stem cells or stem cell-derived transplants towards a motor neuron phenotype.

EXAMPLE 2

MNTF Induced Differentiation in the Presence of SHH Inhibitor

The following example demonstrates the independence of MNTF-induced differentiation from the Shh pathway.
A. Materials and Methods
 1. Materials
 Cyclopamine-KAAD [3-keto-N-(aminoethyl-aminocaproyl-dihydrocinnamoyl)cyclopamine], which inhibits the Shh pathway at the smoothened receptor, was obtained from Calbiochem.
 2. Experimental Protocol
 The ES cells were differentiated as mentioned above and at day 0 they were treated with RA+Shh-Agonist; RA+Shh Agonist+Cyclopamine-KAAD (5 μM); RA+MNTF (33mer at 10 μg/ul); and RA+Cyclopamine-KAAD (5 μM)+MNTF (33mer at 10 μg/ul). The inhibitor was pretreated for an hour before the addition of the other components.
 3. Assay
 At day 5 of differentiation the embryoid bodies were checked for GFP fluoresence indicating the differentiation of the ES cells into a motor neuron phenotype.
B. Results
 Cyclopamine-KAAD (5 μM) blocked the GFP fluorescence effect of Shh-Agonist on mouse ES cells but did not block MNTF induced differentiation of ES cells.
C. Conclusions
 These results show MNTF1 induces differentiation of ES cells into motor neurons through a pathway that is independent from the Sonic Hedgehog signal transduction pathway.

EXAMPLE 3

Autophosporylation of Insulin/IGF Receptor(s) in Response to MNTF

A. Materials and Methods
 1. Materials
 HNMPA-(AM)3 (Hydroxy-2-naphthalenylmethylphosphonic acid trisacetoxymethyl ester), a non-specific inhibitor of insulin receptor (IR), was obtained from Alexis Biochemicals. Rabbit (polyclonal) Anti-Insulin/Insulin Growth Factor-1 Receptor (IR/IGF1R) [pYpY$^{1162/1163}$] Phosphospecific Antibody was obtained from Biosource International (Camarillo, Calif.).
 2. Experimental Protocol
 Embryoid bodies (EBs) were exposed to RA (1 μM)+MNTF 33mer (10 μg/ml) or RA (1 μM)+MNTF 33mer (10 μg/ml)+/−HNMPA-(AM)3 (50 nM). Cells were harvested at 0, 15 min, 30 min, 1 h, 2 h and 4 h time points.

3. Western Blot

The cells were harvested as described previously [Barber, A. J. et al., (2001) J. Biol. Chem. 276, 32814-32821]. Protein concentrations were measured with the Pierce BCA reagent, and all samples were adjusted for equal protein before SDS-polyacrylamide gel electrophoresis.

Cell lysates were immunoblotted with polyclonal antibodies against phosphotyrosines 1162-1163 of IR/IGFR1 following the manufacturer's directions or standard techniques. Protein bands were detected by enhanced chemical fluorescence. Densitometric analysis of enhanced chemical fluorescence immunoblots was performed with ImageQuant (Molecular Dynamics, Sunnyvale, Calif.).

B. Results

FIG. 3 shows autophosphorylation of IR/IGF-R in cells treated with MNTF 33mer and reduced autophosphorylation within 15 min of treatment with the IR inhibitor.

C. Conclusions

MNTF1 treatment initiates the activation of IR/IGF-R mediated signal transduction pathways.

EXAMPLE 4

MNTF Analogs Enhance Survival of Stem Cell Derived Motor Neurons

Survival of ES-derived motor neurons has been shown by others to be dependent on neurotrophic factors, such as NT3, BDNF, CNTF and GDNF. For example, see U.S. patent application Ser. No. 10/196,882, incorporated herein by reference. The following example discloses how MNTF peptides can be used to enhance the survival of stem cell derived motor neurons.

A. Materials and Methods

1. Materials

Retinoic Acid (RA) was obtained from Sigma (R-2625). Sonic hedgehog (Shh) agonist, Hh-Ag1.3, was obtained from Curis, Inc. (Cambridge, Mass.). MNTF 6-mer, 7-mer, 10-mer, 11-mer, 21-mer, and 33-mer peptides were obtained by from CS Bio Company (Menlo Park, Calif.), who produced the peptides by solid phase synthesis in accordance with amino acid sequence information provided by Genervon Biopharmaceuticals LLC (Montebello, Calif.). GDNF and NT3 can be obtained from R&D Systems (Minneapolis, Minn.) and dbcAMP is available from Roche Molecular Biochemicals (Indianapolis, Ind.).

GDNF, dbcAMP, NT3.

2. Experimental Protocol

Mouse embryonic stem (ES) cells were differentiated in the presence of RA and Hg-agonist (Curis, Inc.). On day four, the differentiated embryoid bodies were partially dissociated with 0.05% trypsin or Collagenase and Dispase (1 mg/ml in PBS) and plated on coverslips coated with PLL-Laminin and matrigel.

The dissociated cultures were then treated with GDNF (10 ng/ml), MNTF (all seven forms) at different doses (0.1 µg/ml, 1 µg/ml, 10 µg/ml and 50 µg/ml), and dbcAMP (1 µM), NT3 (10 µg/ml) at day five.

3. Assays

Neurons and their axons were identified by using the fluorescence produced by GFP expressed from the HB9 promoter. Neurite outgrowth can be quantified as described previously [Harper, J. M. et al. (2004) PNAS 101, 7123-7128, incorporated herein by reference] at day six, eight and ten. Percentage survivability was calculated on day ten by counting the total number of cells with existing axons.

B. Results

MNTF 10 and 33 mer were effective at maintaining dissociated cultures up to 10 days in culture. As seen in FIG. 4, the MNTF1 peptides are comparable to a potent motoneuron trophic factor like GDNF, and possibly even better at enhancing survival when compared to NT3 and dbcAMP.

C. Conclusions

MNTF peptide analogs provide an additional growth supplement for ES cell-derived motor neuron cell cultures and may enhance survival of transplanted ES cells in vivo.

EXAMPLE 5

Stem Cell Preparation and Maintenance

A. Preparation of Human Embryonic Stem Cells

Embryonic stem cells can be isolated from blastocysts of members of the primate species (see Thomson et al., *Proc. Natl. Acad. Sci.* USA 92:7844 (1995). Human embryonic stem (hES) cells can be prepared from human blastocyst cells using the techniques described by Thomson et al. (see U.S. Pat. No. 5,843,780; *Science* 282:1145 (1998); *Curr. Top. Dev. Biol.* 38:133 ff. (1998) and Reubinoff et al, *Nature Biotech.* 18:399 (2000). For example, human blastocysts can be obtained from human in vivo preimplantation embryos. Alternatively, in vitro fertilized (IVF) embryos can be used, or one-cell human embryos can be expanded to the blastocyst stage (Bongso et al., *Hum Reprod* 4: 706 (1989). In one suitable approach, embryos are cultured to the blastocyst stage in G1.2 and G2.2 medium (Gardner et al., *Fertil. Steril.* 69:84 (1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., *Proc. Natl. Acad. Sci. USA* 72:5099 (1975). Cells are removed from the intact inner cell mass (ICM) by gentle pipetting after two further washes in DMEM, lysed trophectoderm, and the ICM is plated on mEF feeder layers.

Inner cell mass-derived outgrowths are dissociated into clumps after about 9 to 15 days. This can be preformed either by exposure to calcium and magnesium-free phosphate-buffered saline (PBS) with 1 mM EDTA, or by exposure to dispase or trypsin, or by mechanical dissociation with a micropipette and then replated on mEF in fresh medium. Growing colonies that exhibit an undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, followed by exposure to Dulbecco's PBS (containing 2 mM EDTA), exposure to type IV collagenase (about 200 U/mL; Gibco) or by selection of individual colonies by micropipette. Clump sizes of about 50 to 100 cells are optimal.

B. Preparation of Human Embryonic Germ Cells

Human Embryonic Germ (hEG) cells can be prepared from primordial germ cells present in human fetal material which is taken about 8-11 weeks after the last menstrual period. Suitable preparation methods are described in Shamblott et al., *Proc. Natl. Acad. Sci. USA* 95:13726 (1998) and U.S. Pat. No. 6,090,622.

Genital ridges are rinsed with isotonic buffer, then placed into 0.1 mL 0.05% trypsin/0.53 mM sodium EDTA solution (BRL) and cut into <1 mm³ chunks. The tissue is then pipetted through a 100 µL tip to further disaggregate the cells. It is incubated at 37° C. for about 5 min, and then about 3.5 mL EG growth medium is added. EG growth medium may contain the following: DMEM, 4500 mg/L D-glucose, 2200 mg/L mM NaHCO₃; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant bFGF (Genzyme); and 10 .mu.M forskolin (in 10% DMSO).

Alternatively, EG cells are isolated using hyaluronidase/ collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all obtained from Sigma and prepared in EG growth medium). Tissue is minced, incubated 1 h or overnight at 37° C., resuspended in 1-3 mL of EG growth medium, and plated onto a feeder layer.

Ninety-six well tissue culture plates are then prepared with a sub-confluent layer of feeder cells (e.g., STO cells, ATCC No. CRL 1503) which is typically cultured for 3 days in modified EG growth medium free of LIF, bFGF or forskolin, inactivated with 5000 rad gamma-irradiation. About 0.2 mL of primary germ cell (PGC) suspension is added to each of the wells. The first passage is done after 7-10 days in EG growth medium, transferring each well to one well of a 24-well culture dish previously prepared with irradiated STO mouse fibroblasts. The cells are cultured with daily replacement of medium until cell morphology consistent with EG cells is observed, typically after 7-30 days or 1-4 passages.

C. Propagation of pPS Cells in an Undifferentiated State pPS cells can be propagated continuously in culture under conditions that promote proliferation without promoting differentiation. Exemplary serum-containing ES medium has 80% DMEM (such as Knock-Out DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Immediately prior to use, human bFGF is added to 4 ng/mL (WO 99/20741, Geron Corp.).

Traditionally, ES cells are cultured on a layer of feeder cells (e.g. fibroblasts derived from embryonic or fetal tissue). Embryos are harvested from a CF1 mouse after 13 days of pregnancy, transferred to 2 mL trypsin/EDTA, minced, and incubated 5 min at 37° C. 10% FBS is added, the debris is allowed to settle, and the cells are propagated in 90% DMEM, 10% FBS, and 2 mM glutamine. To prepare a feeder cell layer, cells are irradiated to inhibit proliferation but permit synthesis of factors that support ES cells (approximately 4000 rads gamma-irradiation). Culture plates are coated with 0.5% gelatin overnight, plated with 375,000 irradiated mEFs per well, and used between 5 h to 4 days after plating. The medium is replaced with fresh hES medium just prior to seeding the pPS cells.

Feeder-free cultures are supported in a nutrient medium and are typically conditioned by culturing irradiated primary mouse embryonic fibroblasts, telomerized mouse fibroblasts, or fibroblast-like cells derived from pPS cells. The medium can be conditioned by plating the feeders at a density of about 5-6 times 10⁴ cm² in a serum free medium such as KO DMEM which is supplemented with 20% serum replacement and 4 ng/mL bFGF. Medium that has been conditioned for 1-2 days is supplemented with further bFGF, and used to support pPS cell culture for 1-2 days.

ES cells appear with high nuclear/cytoplasmic ratios, prominent nucleoli, and compact colony formation with poorly discernable cell junctions. Primate ES cells express stage-specific embryonic antigens (SSEA3 and SSEA4), and markers that are detectable using antibodies designated Tra-1-60 and Tra-1-81 (Thomson et al., Science 282:1145, 1998). Mouse ES cells can be used as a positive control for SSEA-1, and as a negative control for SSEA-4, Tra-1-60, and Tra-1-81. SSEA-4 is consistently present on human embryonal carcinoma (hEC) cells. Differentiation of pPS cells in vitro results in the loss of SSEA-4, Tra-1-60, and Tra-1-81 expression and increased expression of SSEA-1. SSEA-1 is also found on hEG cells.

D. Preparing Neural Precursors and Terminally Differentiated Cells

Certain neural precursor cells provided herein are obtained by culturing, differentiating, or programming stem cells in a particular culture environment that enriches for cells with a desired phenotype. These methods are applicable to many types of stem cells, including primate pluripotent stem (pPS) cells described herein. Neuronal cell differentiation generally takes place in a culture environment comprising a suitable substrate and a nutrient medium containing differentiation agents are added. Suitable substrates include solid surfaces coated with a positive charge, such as a basic amino acid, exemplified by poly L-lysine and polyornithine. Substrates can be coated with extracellular matrix components, exemplified by fibronectin. Other permissive extracellular matrixes include Matrigel® (extracellular matrix from Engelbreth-Holm-Swarm tumor cells), laminin, and combination substrates, such as poly-L-lysine combined with fibronectin, laminin, or both.

Differentiated cells can be sorted based on phenotypic features to enrich for certain populations. Cell sorting can be performed by contacting cells in a population with an antibody or ligand that binds to a marker characteristic of neural cells, followed by separation of the specifically recognized cells from other cells in the population. One method is immunopanning, in which specific antibody is coupled to a solid surface. The cells are contacted with the surface, and cells not expressing the marker are washed away. The bound cells are then recovered by more vigorous elution. Variations of this are affinity chromatography and antibody-mediated magnetic cell sorting. In a typical sorting procedure, the cells are contacted with a specific primary antibody, and then captured with a secondary anti-immunoglobulin reagent bound to a magnetic bead which can be subjected to a magnetic field to recover adherent cells.

Another suitable method of separation is fluorescence-activated cell sorting, where cells expressing the marker are labeled with a specific antibody (e.g. via a fluorescently labeled secondary anti-immunoglobulin) and separated according to the amount of bound label using a suitable sorting instrument. Any of these methods are suitable to permit isolation and recovery of a positively selected population of cells that have the marker of interest, and a negatively selected population of cells that not have the particular marker in sufficient density or accessibility to be positively selected. Negative selection can also be performed by incubating the cells successively with a specific antibody to produce a population cells that will lyse when the antibody has bound in the presence of a complement preparation. Sorting of the differentiated cell population can occur at any time, but preferably shortly after initiating the differentiation process.

Cells can be characterized according to a number of phenotypic criteria. The criteria include but are not limited to microscopic observation of morphological features, detection or quantitation of expressed cell markers, enzymatic activity, or neurotransmitters and their receptors, and electrophysiological function.

Certain cells embodied in this invention have morphological features characteristic of neuronal cells or glial cells. The features are readily appreciated by those skilled in evaluating the presence of such cells. For example, characteristic of neurons are small cell bodies, and multiple processes reminiscent of axons and dendrites. Cells of this invention can also be characterized according to whether they express phenotypic markers characteristic of neural cells of various kinds.

Suitable markers include but are not limited to β-tubulin III, microtubule-associated protein 2 (MAP-2), or neurofilament, characteristic of neurons; glial fibrillary acidic protein (GFAP), present in astrocytes; galactocerebroside (GalC) or myelin basic protein (MBP), characteristic of oligodendrocytes; Oct-4, characteristic of undifferentiated hES cells; Nestin, characteristic of neural precursors and other cells; and both A2B5 and polysialylated NCAM (these markers can sometimes be displayed on other cell types, such as liver or muscle cells). β-Tubulin III was previously thought to be specific for neural cells, but it has been discovered that a subpopulation of hES cells is also β-tubulin III positive. MAP-2 is a more stringent marker for fully differentiated neurons of various types.

Tissue-specific markers described herein or known in the art can be detected using known immunological techniques, including for example flow immunocytochemistry for cell-surface markers, immunohistochemistry (for example, of fixed cells or tissue sections) for intracellular or cell-surface markers, Western blot analysis of cellular extracts, and enzyme-linked immunoassay (e.g. an enzyme linked immunosorbent assay (ELISA)), for cellular extracts or products secreted into the medium. Expression of an antigen by a cell is said to be "antibody-detectable" if a significantly detectable amount of antibody will bind to the antigen in a standard immunocytochemistry or flow cytometry assay, including after fixation of the cells, and optionally using a labeled secondary antibody or other conjugate (such as a biotin-avidin conjugate) to amplify labeling.

Tissue-specific gene product expression can also be detected at the mRNA level, for example by Northern blot analysis, dot-blot hybridization analysis, or by reverse transcriptase initiated polymerase chain reaction (RT-PCR) (See U.S. Pat. No. 5,843,780). Differentiation of particular neural precursor cell populations of this invention (e.g. using motoneuronotropic factor (MNTF) or an MNTF analogue) can generate cell populations that are at least 20%, 30%, 40%, or more than 50% MAP-2 positive. A substantial proportion, say 5%, 10%, 25%, or more of the NCAM or MAP-2 positive cells will be capable of synthesizing a neurotransmitter, such as acetylcholine, glycine, glutamate, norepinephrine, serotonin, or GABA. Certain populations of cells contain NCAM or MAP-2 positive cells that are 0.1%, and possibly 1%, 3%, or 5% or more (on a cell count basis) that are positive for tyrosine hydroxylase (TH), measured by immunocytochemistry or mRNA expression. This generally considered in the art to be a marker for dopamine synthesizing cells.

EXAMPLE 6

Differentiation of Murine Embryonic Stem Cells into Motoneurons by MNTF

In this example, we show here that a synthetic 33mer MNTF peptide (SEQ ID NO:1) and a 10mer MNTF peptide (SEQ ID NO:4) effectively substitute for Sonic Hedgehog in the differentiation of murine ES cells in vitro into motor neurons in the presence of Retinoic Acid.

Figure 5:
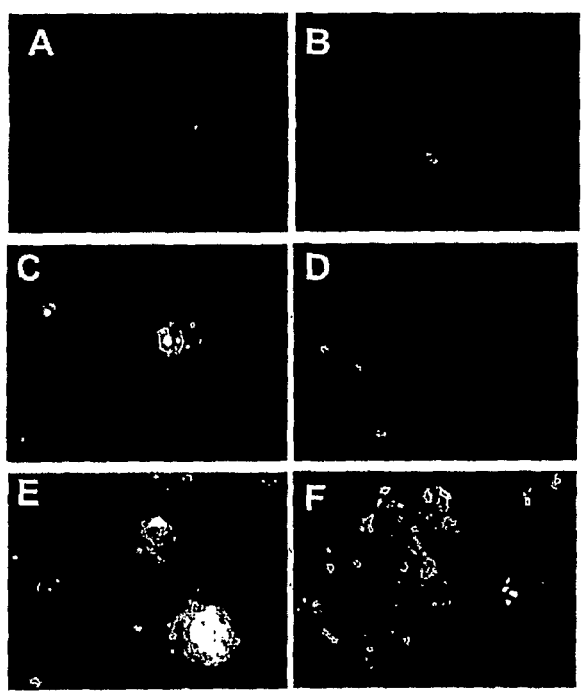
FIG. 5 illustrates a comparison of the expression of GFP fluorescence under the control of the motor neuron specific HB9 promoter at day 5 of differentiation in response to control (A), RA (B); RA/Shh (C); cyclopamine-KAAD, RA/Shh (D); RA and MNTF 33mer (SEQ ID NO:1) (E); Cyclopamine-KAAD, RA and MNTF 33mer (SEQ ID NO:1) (F)

Receptor kinase studies were used to measure the affinity of MNTF for the Insulin Receptor (IR). The results showed that MNTF has affinity for the Insulin Receptor (IR) and the Insulin-like growth Factor Receptor (IGF-1R). We then tested whether signals through either of these pathways are possible in generating motor neurons. FIG. 5 shows that cyclopamine-KAAD (5 uM), a specific inhibitor of smoothened receptor signaling, blocks the effect of Shh on mouse ES cells but did not block the activity of MNTF induced differentiation on the ES cells. Thus, MNTF is still capable of generating postmitotic mature motor neurons.

FIG. 5 illustrates a comparison of the expression of GFP fluorescence under the control of the motor neuron specific HB9 promoter at day 5 of differentiation in response to control (A), RA (3); RA/Shh (C); cyclopamine-KAAD, RA/Shh (D); RA and MNTF 33mer (E); Cyclopamine-KAAD, RA and MNTF 33mer (F). This data indicates that MNTF signals either i) through an entirely different pathway than Shh, or ii) that the two pathways converge downstream of smoothened.

Figure 6:
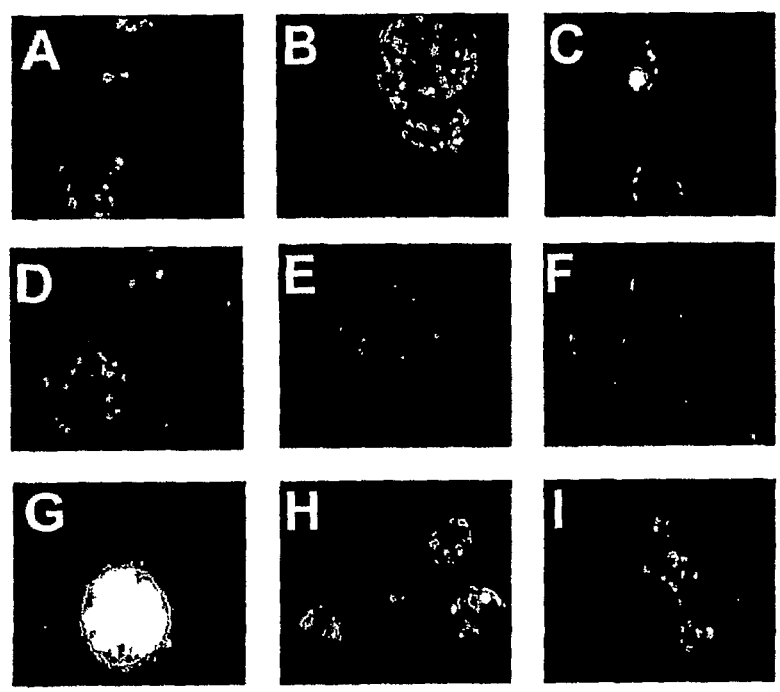
FIG. 6 shows that IGF1-R inhibitor picrodophyllin does not effectively block the activity of MNTF induced differentiation as indicated by the expression of GFP fluorescence of day 5 embryoid bodies in response to RA/Shh (A); RA/MNTF33(B); RA/MNTF10 (C); HNMPA(AM)3 (15 μM)/Shh (D); HNMPA(AM)3/MNTF33 (E); HNMPA(AM)3/MNTF10 (F); PPP (1 μM), RA/Shh (G); PPP (1 μM), RA/MNTF33 (H); PPP (1 μM), RA/MNTF10 (I)

FIG. 6 shows that the insulin receptor-specific tyrosine kinase inhibitor HNMPA(AM)3 blocks the effect of MNTF on mouse ES cells but did not block the activity of Shh induced differentiation on the ES cells. The IGF1-R inhibitor picrodophyllin does not effectively block the activity of MNTF induced differentiation as indicated by the expression of GFP fluorescence of day 5 embryoid bodies in response to RA/Shh (A); RA/MNTF33(B); RA/MNTF10 (C); HNMPA (AM)3 (15 μM)/Shh (D); HNMPA(AM)3/MNTF33 (E); HNMPA(AM)3/MNTF10(F); PPP (1 μM), RA/Shh (G); PPP (1 μM), RA/MNTF33 (H); PPP (1 μM), RA/MNTF10 (I). MNTF treatment of ES cells resulted in the auto-phosphorylation of Tyr972 and Tyr 1162/1163, which is a marker of IR activation.

Immunoprecipitation:

Co-immunoprecipitation studies were also performed. Postnuclear supernatants from insulin-stimulated, IGF-I stimulated, or MNTF-33mer (10 ug/ml) day 0 ES cells were normalized for amounts of total protein (8 mg). Lysates were incubated for 4 h at 4° C. with 5-μg anti-IRS-1 antibody, and the immunocomplexes were captured by addition of 30 μl 50% protein-A agarose slurry. After four washes with cold lysis buffer, pellets were resuspended in SDS-PAGE sample buffer and boiled for 5 min. Proteins were resolved by SDS-PAGE (10%) and transferred by electroblotting onto PVDF membrane. The membrane was incubated in blocking solution (TBST, 3% dry milk) for 1 h at room temperature followed by incubation with one of the following antibodies: anti-PI-3 kinase p85 subunit ((1 μg/ml in TBST, 3% milk, overnight at 4° C.). Proteins were transferred to Immobilon-P transfer membranes (Millipore, Bedford, Mass.) in 20% methanol transfer buffer. The western blots were developed with the SuperSignal West Femto Maximum Sensitivity Substrate (Pierce, Rockford, Ill.) and visualized with a Fuji Luminescent Image Analyzer (LAS-1000plus camera; Fuji, Tokyo, Japan). The intensity of each band was determined by Image Gauge software (version 3.4).

The co-immunoprecipitation studies showed the association of specific SH2 domains with IR (p85 subunit for PI3kinase) resulted from MNTF treatment on the ES cells.

The data presented herein further shows that blocking IGF-1R had no effect on the ability of MNTF to generate motor neurons, but that blocking IR abolished this ability. These results support the idea that MNTF is a novel factor capable of generating and supporting motor neurons through a Shh-independent, IR dependent pathway.

Figure 7:
FIG. 7 illustrates a western blot using antibody to the p85 subunit of PI3-kinase from ES cell lysates from cells treated with IGF-1 (10 nM) (Lane 1), Insulin (100 nM) (Lane 2), MNTF6 (Lane 3), MNTF 10 (Lane 4), and MNTF33 (Lane 5) for 5 minutes. Lysates were then incubated with protein A beads and anti-IRS-1 antibody. Immunocomplexes were fractionated by SDS-PAGE (10%), transferred to membrane, and analyzed by western blot using antibody to the p85 subunit of PI3-kinase.

Signal Transduction of MNTF—Biochemical Approach:

The purpose of this experiment was to confirm the signaling of MNTF through the Insulin Receptor. FIG. 7 shows the results of an experiment in which ES cells were treated with IGF-1 (10 nM) (Lane 1), Insulin (100 nM) (Lane 2), MNTF6 (Lane 3), MNTF 10 (Lane 4), and MNTF33 (Lane 5) for 5 minutes. Lysates were then incubated with protein A beads and anti-IRS-1 antibody. Immunocomplexes were fractionated by SDS-PAGE (10%), transferred to membrane, and analyzed by western blot using antibody to the p85 subunit of PI3-kinase. Lysates were then incubated with protein A beads and anti-IRS-1 antibody. Immunocomplexes were fractionated by SDS-PAGE (10%), transferred to membrane, and analyzed by western blot using antibody to the p85 subunit of PI3-kinase.

There are differences between the IR and IGF-IR receptors with regard to the complement of SH2-containing proteins recruited to IRS-1. In particular, IGF-IR appears to couple IRS-1 preferentially to Grb2 whereas, in contrast, IR appears to couple IRS-1 preferentially to the p85 subunit of phosphatidyl inositol 3-kinase (PI3-kinase) and to Nck. The two receptors couple IRS-1 equally to the tyrosine phosphatase SBP2. There are three important tyrosine phosphorylation sites on IRS-1 (pY608, pY895 and pY1172). In the case of pY608, Amoui et al. showed evidence for differential phosphorylation of IRS-1 by the two receptors i.e. Y608 is more phosphorylated in IGF1-R stimulated cells. Amoui et al., *J. Endocrinology.*, 171(1):153-62 (2001).

These results support the idea that the cytoplasmic domains of IR and IGF-IR have differences in their intrinsic signaling potentials. With this in mind, the ES cells are induced with MNTF in a serum free environment and the lysates are co-immunoprecipitated with anti-IRS-1 and its corresponding SH2 domains, e.g. p85 subunit of PI3K and Grb2 respectively.

A. Common Convergence of Shh and MNTF Pathway.

Figure 8:
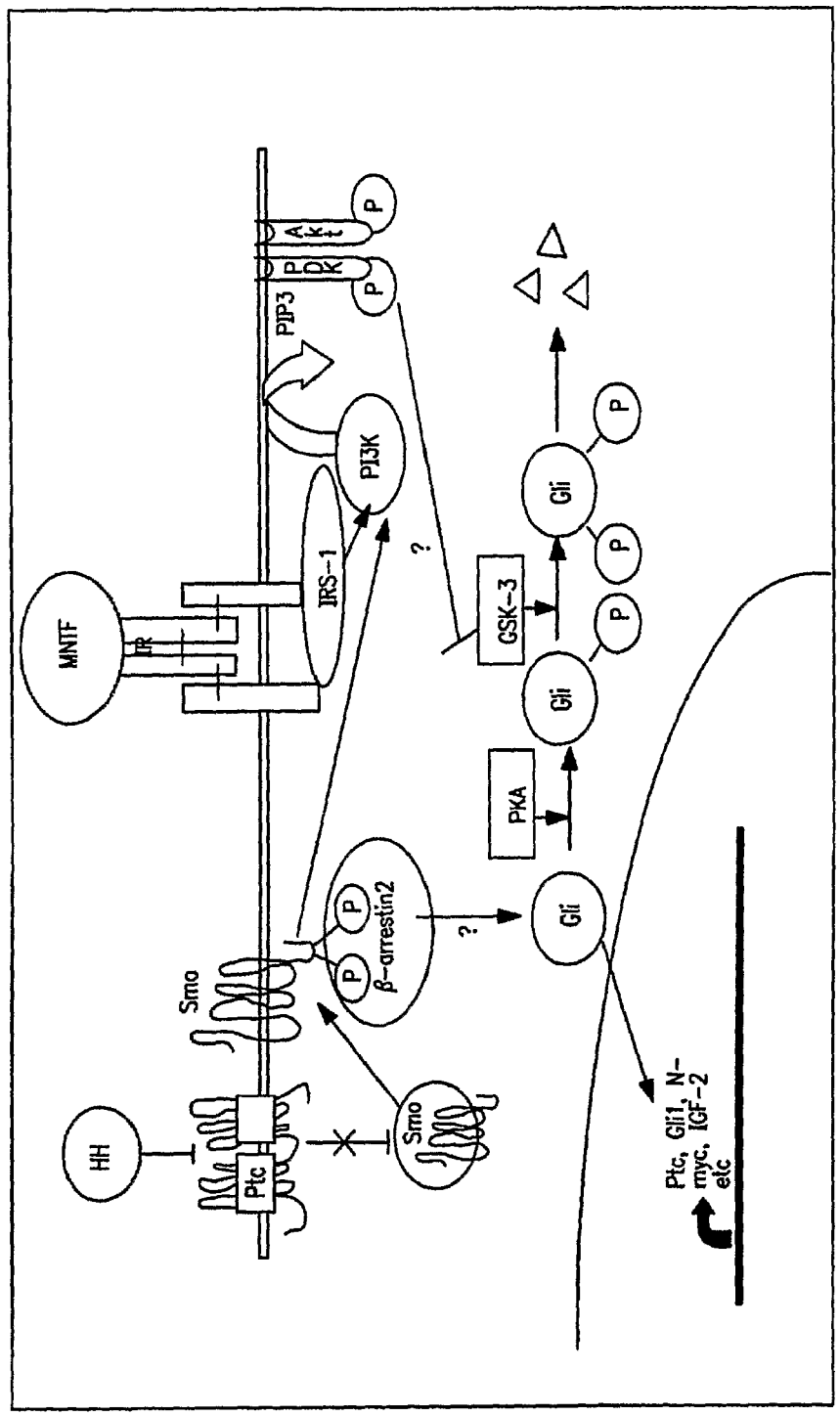
FIG. 8 illustrates a possible pathway for MNTF induced differentiation of ES cells.

The purpose of this experiment was to determine a common downstream effector of Shh and MNTF signaling. It was recently noted that Phosphoinositide 3-kinase (PI3-kinase)-dependent Akt activation is essential for Sonic Hedgehog (Shh) signaling in the specification of neuronal fates in chicken neural explants, chondrogenic differentiation of 10T1_2 cells, and Gli activation in NIH 3T3 cells. Riobo N A, et al., P.N.A.S. USA. 103(12):4505-10 (2006). Stimulation of PI3-kinase_Akt by insulin-like growth factor I potentiates Gli activation induced by low levels of Shh; however, insulin-like growth factor I alone is insufficient to induce Gli-dependent transcription. Protein kinase A (PKA) and glycogen synthase kinase 3_sequentially phosphorylate Gli2 at multiple sites, identified by mutagenesis, thus resulting in a reduction of its transcriptional activity. Gli2 mutant proteins in which the major PKA and glycogen synthase kinase 3_phosphorylation sites were mutated to alanine remain fully transcriptionally active; however, PKA-mutant Gli2 functions independently of Akt signaling, indicating that Akt positively regulates Shh signaling by controlling PKA-mediated Gli inactivation. FIG. 8 illustrates a possible pathway for MNTF induced differentiation of ES cells.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for differentiating mouse embryonic stem cells or mouse pluripotent stem cells, said method comprising i) obtaining a population of mouse embryonic stem cells or mouse pluripotent stem cells; ii) culturing the population of mouse embryonic stem cells or mouse pluripotent stem cells in a differentiating medium comprising a motoneuronotrophic factor (MNTF) analogue having the amino acid sequence of SEQ ID NO:1 or SEQ ID NO:4 and retinoic acid to induce differentiation into neurons; iii) inducing proliferation of the neurons; and, optionally iv) transplanting the neurons to said host.

2. The method of claim 1 comprising transplanting the neurons into a host having a neuronal disorder, wherein the neuronal disorder is treated.

3. The method of claim 2 wherein said MNTF analogue acts as a neuroprotective agent.

4. The method of claim 2 wherein administering said MNTF analogue ameliorates or inhibits the progression of the neuronal disorder.

5. The method of claim 2 wherein a protein kinase pathway is modulated by a sonic hedgehog independent pathway to ameliorate or inhibit the progression of said neuronal disorder.

6. The method of claim 2 wherein said MNTF analogue is capable of stimulating the autophosphorylation of Tyr972 and Tyr1162/1163 of the insulin receptor in vitro.

7. The method of claim 2 wherein said MNTF analogue modulates the expression or activity of one or more proteins selected from a tyrosine kinase, a growth factor, a insulin receptor, IGF-1 receptor, IGF-2 receptor, Shh, Akt, Bad (bcl-2 antagonist of cell death), PI(3,4,5)P3-dependent kinase 1 (PDK1), Bax, p53 gene product, pp60-Src, JAK2, nitric oxide synthases (NOS), glycogen synthase kinase 3 (GSK), caspase, PI3 kinase (phosphatidylinositol 3-kinase), and Ras.

8. The method of claim 2 wherein said motoneuronotropic factor (MNTF) analogue modulates the expression or activity of one or more proteins which bind to tyrosine-phosphorylated IRS-protein, wherein said one or more proteins are selected from IRS-1, IRS-2, IRS-4, P13 Kinase, p85, P110, GRB2, SHP2, Nck, Crk, Fyn, Insulin receptor, IGF-1 receptor, and IGF-2 receptor.

9. The method of claim 2 wherein the survival and/or maintenance of embryonic stem cell progeny or pluripotent stem cell progeny, neuronal progenitor cells and/or neurons is enhanced.

10. The method of claim 2 wherein said neurons are motor neurons.

11. The method of claim 1, wherein said population of stem cells is cultured with retinoic acid before said MNTF analogue.

12. The method of claim 1, wherein said motoneuronotrophic factor (MNTF) analogue has an amino acid sequence consisting of SEQ ID NO:1 or SEQ ID NO:4.

13. The method of claim 1 wherein said motoneuronotrophic factor (MNTF) analogue has an amino acid sequence consisting of SEQ ID NO:1.

14. The method of claim 1 wherein said motoneuronotrophic factor (MNTF) analogue has an amino acid sequence consisting of SEQ ID NO:4.

15. The method of claim 1 wherein said retinoic acid, is added to the culture medium in an amount sufficient to neuralize and to establish a caudal positional identity for pluripotent cells.

16. The method of claim 1 wherein the motoneuronotrophic factor (MNTF) analogue is present in the culture medium in an amount from about 0.1 µg/ml to about 50 µg/ml.

17. The method of claim 1 wherein the motoneuronotrophic factor (MNTF) analogue is present in the culture medium in an amount from about 0.1 µg/ml to about 10 µg/ml.

18. The method of claim 1 wherein the population comprises embryonic stem cells.

19. The method of claim 1 wherein the population comprises pluripotent stem cells.

20. The method of claim 1 wherein said retinoic acid is present in an amount from about 0.1 µg/ml to about 150 µg/ml.

21. The method of claim 1, comprising the step of transplanting the neurons to said host after step iv).

22. A method for differentiating mouse embryonic stem cells or mouse pluripotent stem cells and transplanting the progeny to a host, said method comprising i) obtaining a population of mouse embryonic stem cells or mouse pluripotent stem cells; ii) culturing the population of mouse embryonic stem cells or mouse pluripotent stem cells in a differentiating medium until the population differentiates into embryoid bodies, iii) culturing the embryoid bodies in a culture medium comprising a motoneuronotrophic factor (MNTF) analogue having the amino acid sequence of SEQ ID NO:1 or SEQ ID NO:4 and retinoic acid to induce differentiation of the embryoid bodies into neurons; iv) inducing proliferation of the neurons; and, optionally) transplanting the neurons to said host.

* * * * *